United States Patent
Harlev et al.

(10) Patent No.: US 9,113,809 B2
(45) Date of Patent: Aug. 25, 2015

(54) IMPEDANCE BASED ANATOMY GENERATION

(75) Inventors: Doron Harlev, Boston, MA (US); Alpar Csendes, Burlington, MA (US); Zsolt Badics, Andover, MA (US)

(73) Assignee: Rhythmia Medical, Inc., Burlington, MA (US)

( * ) Notice: Subject to any disclaimer, the term of this patent is extended or adjusted under 35 U.S.C. 154(b) by 859 days.

(21) Appl. No.: 13/354,750

(22) Filed: Jan. 20, 2012

(65) Prior Publication Data

US 2012/0130267 A1    May 24, 2012

Related U.S. Application Data

(63) Continuation of application No. 12/438,794, filed on May 8, 2009, now Pat. No. 8,103,338.

(51) Int. Cl.
*A61B 5/053* (2006.01)
*A61B 5/00* (2006.01)
*A61B 5/042* (2006.01)
*A61B 6/00* (2006.01)
*A61B 8/08* (2006.01)

(52) U.S. Cl.
CPC .............. *A61B 5/0537* (2013.01); *A61B 5/0536* (2013.01); *A61B 5/4869* (2013.01); *A61B 5/6858* (2013.01); *A61B 5/042* (2013.01); *A61B 6/503* (2013.01); *A61B 8/0883* (2013.01)

(58) Field of Classification Search
CPC ...... A61B 5/042; A61B 5/0422; A61B 5/053; A61B 5/0536; A61B 5/063; A61B 6/503; A61B 8/0883

USPC .......................... 600/547, 549, 523, 529, 544
See application file for complete search history.

(56) References Cited

U.S. PATENT DOCUMENTS

| | | |
|---|---|---|
| 4,649,924 A | 3/1987 | Taccardi |
| 4,674,518 A | 6/1987 | Salo ............................... 128/695 |
| 4,840,182 A | 6/1989 | Carlson ......................... 128/694 |
| 4,920,490 A | 4/1990 | Isaacson ................... 364/413.13 |
| 5,156,151 A | 10/1992 | Imran |
| 5,284,142 A | 2/1994 | Goble et al. ................ 128/653.1 |
| 5,297,549 A | 3/1994 | Beatty et al. |
| 5,300,068 A | 4/1994 | Rosar et al. ...................... 606/34 |
| 5,341,807 A | 8/1994 | Nardella |
| 5,381,333 A | 1/1995 | Isaacson et al. .......... 364/413.13 |
| 5,469,858 A | 11/1995 | Osborne |
| 5,480,422 A | 1/1996 | Ben-Haim |
| 5,500,011 A | 3/1996 | Desai |
| 5,553,611 A | 9/1996 | Budd et al. ..................... 128/642 |
| 5,568,809 A | 10/1996 | Ben-Haim |
| 5,577,502 A | 11/1996 | Darrow et al. ............. 128/653.1 |
| 5,588,429 A | 12/1996 | Isaacson et al. |
| 5,634,469 A | 6/1997 | Bruder et al. |
| 5,662,108 A | 9/1997 | Budd et al. |
| 5,687,737 A | 11/1997 | Branham et al. |

(Continued)

OTHER PUBLICATIONS

Authorized officer Athina Nickitas-Etienne, International Preliminary Report on Patentability in PCT/US2010/027436 mailed Nov. 17, 2011, 5 pages.

(Continued)

*Primary Examiner* — Max Hindenburg
(74) *Attorney, Agent, or Firm* — Faegre Baker Daniels LLP

(57) ABSTRACT

Methods and systems for the determination and representation of a chamber anatomy are disclosed herein.

34 Claims, 11 Drawing Sheets

(56) References Cited

U.S. PATENT DOCUMENTS

| | | | |
|---|---|---|---|
| 5,697,377 A | 12/1997 | Wittkampf | |
| 5,704,365 A | 1/1998 | Albrecht et al. | |
| 5,722,402 A | 3/1998 | Swanson et al. | 128/642 |
| 5,840,025 A | 11/1998 | Ben-Haim | |
| 5,840,031 A | 11/1998 | Crowley | |
| 5,846,198 A | 12/1998 | Killmann | 600/424 |
| 5,848,972 A | 12/1998 | Triedman et al. | |
| 5,921,982 A | 7/1999 | Lesh et al. | 66/41 |
| 5,954,665 A | 9/1999 | Ben-Haim | |
| 5,971,933 A | 10/1999 | Gopakumaran et al. | 600/526 |
| 5,983,126 A | 11/1999 | Wittkampf | |
| 6,014,581 A | 1/2000 | Whayne et al. | |
| 6,050,267 A | 4/2000 | Nardella et al. | |
| 6,095,150 A | 8/2000 | Panescu et al. | 128/899 |
| 6,167,296 A | 12/2000 | Shahidi | |
| 6,226,542 B1 | 5/2001 | Reisfeld | 600/407 |
| 6,236,886 B1 | 5/2001 | Cherepenin et al. | |
| 6,240,307 B1 | 5/2001 | Beatty et al. | |
| 6,246,898 B1 | 6/2001 | Vesely et al. | |
| 6,254,536 B1 | 7/2001 | DeVito | 600/300 |
| 6,278,894 B1 | 8/2001 | Salo et al. | 600/547 |
| 6,298,257 B1 | 10/2001 | Hall et al. | 600/407 |
| 6,308,093 B1 | 10/2001 | Armoundas et al. | 600/509 |
| 6,314,310 B1 | 11/2001 | Ben-Haim et al. | |
| 6,317,619 B1 | 11/2001 | Boernert et al. | 600/410 |
| 6,318,375 B1 | 11/2001 | Plicchi et al. | 128/899 |
| 6,360,123 B1 | 3/2002 | Kimchi et al. | 600/547 |
| 6,368,285 B1 | 4/2002 | Osadchy et al. | 600/508 |
| 6,400,981 B1 | 6/2002 | Govari | |
| 6,490,474 B1* | 12/2002 | Willis et al. | 600/424 |
| 6,516,807 B1 | 2/2003 | Panescu et al. | |
| 6,547,082 B1 | 4/2003 | Babini | 211/41.17 |
| 6,556,695 B1 | 4/2003 | Packer et al. | |
| 6,574,492 B1 | 6/2003 | Ben-Haim et al. | |
| 6,574,498 B1 | 6/2003 | Gilboa | 600/424 |
| 6,593,884 B1 | 7/2003 | Gilboa et al. | |
| 6,600,948 B2 | 7/2003 | Ben-Haim et al. | |
| 6,603,996 B1 | 8/2003 | Beatty et al. | |
| 6,631,290 B1 | 10/2003 | Guck et al. | |
| 6,640,119 B1 | 10/2003 | Budd et al. | 600/374 |
| 6,650,927 B1 | 11/2003 | Keidar | |
| 6,690,963 B2 | 2/2004 | Ben-Haim et al. | |
| 6,701,176 B1 | 3/2004 | Halperin et al. | |
| 6,728,562 B1 | 4/2004 | Budd et al. | |
| 6,773,402 B2 | 8/2004 | Govari et al. | |
| 6,807,439 B2 | 10/2004 | Edwards et al. | 600/420 |
| 6,839,588 B1 | 1/2005 | Rudy | |
| 6,847,839 B2 | 1/2005 | Ciaccio et al. | |
| 6,872,428 B2 | 3/2005 | Yang et al. | 427/568 |
| 6,892,090 B2 | 5/2005 | Verard et al. | 600/424 |
| 6,892,091 B1 | 5/2005 | Ben-Haim et al. | 600/509 |
| 6,939,309 B1 | 9/2005 | Beatty et al. | 600/508 |
| 6,957,101 B2 | 10/2005 | Porath et al. | |
| 6,978,168 B2 | 12/2005 | Beatty et al. | |
| 6,990,370 B1 | 1/2006 | Beatty et al. | 600/509 |
| 7,016,719 B2 | 3/2006 | Rudy et al. | |
| 7,043,292 B2 | 5/2006 | Tarjan et al. | |
| 7,263,397 B2 | 8/2007 | Hauck et al. | 600/374 |
| 7,505,810 B2 | 3/2009 | Harlev et al. | 600/509 |
| 7,515,954 B2 | 4/2009 | Harlev et al. | |
| 7,729,752 B2 | 6/2010 | Harlev et al. | |
| 8,137,343 B2 | 3/2012 | Harlev et al. | |
| 2002/0151807 A1 | 10/2002 | Goldin | |
| 2003/0018251 A1 | 1/2003 | Solomon | |
| 2003/0065271 A1 | 4/2003 | Khoury | |
| 2003/0076277 A1 | 4/2003 | Muramatsu et al. | 345/1.1 |
| 2003/0078509 A1 | 4/2003 | Panescu | |
| 2003/0216630 A1 | 11/2003 | Jersey-Willuhn et al. | |
| 2004/0077942 A1 | 4/2004 | Hall et al. | 600/428 |
| 2004/0097806 A1 | 5/2004 | Hunter et al. | |
| 2004/0243015 A1 | 12/2004 | Smith et al. | |
| 2004/0254437 A1 | 12/2004 | Hauck et al. | |
| 2005/0038337 A1 | 2/2005 | Edwards | 600/424 |
| 2005/0054918 A1 | 3/2005 | Sra | |
| 2005/0107834 A1 | 5/2005 | Freeman et al. | |
| 2005/0154282 A1 | 7/2005 | Li et al. | 600/407 |
| 2005/0288599 A1 | 12/2005 | MacAdam et al. | 600/509 |
| 2006/0085049 A1 | 4/2006 | Cory et al. | 607/48 |
| 2006/0116575 A1 | 6/2006 | Willis | |
| 2006/0122526 A1 | 6/2006 | Berenfeld et al. | |
| 2006/0173251 A1 | 8/2006 | Govari et al. | 600/306 |
| 2006/0178587 A1 | 8/2006 | Khoury | 600/509 |
| 2006/0241401 A1 | 10/2006 | Govari et al. | 600/424 |
| 2007/0016007 A1 | 1/2007 | Govari et al. | 600/424 |
| 2007/0038078 A1 | 2/2007 | Osadchy | 600/424 |
| 2007/0049821 A1 | 3/2007 | Willis | |
| 2007/0197929 A1* | 8/2007 | Porath et al. | 600/523 |
| 2007/0265539 A1 | 11/2007 | Hastings et al. | |
| 2007/0270688 A1* | 11/2007 | Gelbart et al. | 600/427 |
| 2007/0270703 A1 | 11/2007 | He et al. | |
| 2007/0287902 A1 | 12/2007 | Fuimaono et al. | |
| 2007/0299351 A1 | 12/2007 | Harlev et al. | 600/509 |
| 2007/0299352 A1 | 12/2007 | Harlev et al. | |
| 2008/0190438 A1 | 8/2008 | Harlev et al. | |
| 2008/0221566 A1 | 9/2008 | Krishnan | |
| 2008/0234588 A1 | 9/2008 | Feldman et al. | |
| 2008/0249424 A1 | 10/2008 | Harlev et al. | |
| 2009/0171274 A1 | 7/2009 | Harlev et al. | 604/95.04 |
| 2009/0177072 A1 | 7/2009 | Harlev et al. | |
| 2009/0253976 A1 | 10/2009 | Harlev et al. | |
| 2010/0286551 A1 | 11/2010 | Harlev et al. | |

OTHER PUBLICATIONS

E. J. Haug, K. K. Choi, V. Komkov: Design Sensitivity Analysis of Structural Systems, Mathematics in Science and Engineering, vol. 177 (1986).

L. Piegl, W. Tiller: The NURBS Book, 2nd Edition, Springer (1997).

Adams et al., "Seeded Region Growing", *IEEE Transactions on Pattern Analysis and Machine Intelligence*, 16(6):641-647, 1994.

Arthur, "Clinical Use of Intracardiac Impedance: Current Applications and Future Perspectives", PACE, vol. 24:500-506, Apr. 2001.

Authorized officer Sung Chan Chung, International Search Report and Written Opinion in PCT/US2010/027436 mailed Oct. 27, 2010, 10 pages.

Baan, Jan et al., "Continuous Measurement of Left Ventricular Volume in Animals and Humans by Conductance Catheter", *Circulation*, vol. 70,pp. 812-823.

Badics, "Real-Time Reconstruction of Endocardial Potential Maps in Non-Contact Cardiac Mapping", International Journal for computation and Mathematics in Electrical Engineering (COMPEL). vol. 28, No. 4, 2009.

Ben-Haim et al., "Nonfluoroscopic, in Vivo Navigation and Mapping Technology", *Nature Medicine*, 2(12):1393-1395, 1996.

Besl et al., "A Method for Registration of 3-D Shapes", *IEEE Transactions on Pattern Analysis and Machine Intelligenc*, 14(2):239-256, 1992.

Blomström-Lundqvist et al., "ACC/AHA/ESC Guidelines for the Management of Patients with Supraventricular Arrhythmias-Executive Summary", *Journal of the American College of Cardiology*, 42(8):1493-1531, 2003.

Breithardt et al., "AHA Medical/Scientific Statement—Special Report: Standards for Analysis of Ventricular Late Potentials Using High-Resolution of Signal-Averaged Electrocardiography", *Circulation*, 83(4):1481-1488, 1991.

Brooks et al., "Electrical Imaging of the Heart", *IEEE Signal Processing Magazine*, pp. 24-42, 1997.

Caspi et al., "Stem Cell Research: Regenerating the Heart Using Human Embryonic Stem Cells—from Cell to Bedside", *IMAJ*, 8:208-214, 2006.

Cheney et al., "Electrical Impedance Tomography", SIAM Review 41:85-1001, 1999.

De Groot et al., "Three-Dimensional Catheter Positioning During Radiofrequency Ablation in Patients: First Application of a Real-Time Position Management System", *Journal of Cardiovascular Electrophysiology*, 11:1183-1192, 2000.

Donahue et al., "Focal Modification of Electrical Conduction in the Heart by Viral Gene Transfer", *Nature Medicine*, 6(12):1395-1398, 2000.

(56) References Cited

OTHER PUBLICATIONS

Dong et al., "Integrated Electroanatomic Mapping with Three-Dimensional Computer Tomographic Images for Real-Time Guided Ablations", *Circulation*, 113:186-194, 2006.

Durrer et al., "Total Excitation of the Isolation Human Heart", *Circulation*, vol. VLI, pp. 899-912, 1970.

Ector, Joris et al., "Cardiac Three-Dimensional Magnetic Resonance Imaging and Fluoroscopy Merging", *Circulation*, (Dec. 13, 2005).

Fletcher: "Chapter 6 Sums of Squares and Nonlinear Equations", Practical Methods of Optimizations, 2nd Edition, J. Willey & Sons, pp. 110-119, (1987).

Friedman, "Catheter Cryoablation of Cardiac Arrhythmias", *Current Opinion in Cardiology*, 20:48-54, 2005.

Friedman, "Novel Mapping Techniques for Cardiac Electrophysiology", *Heart*, 87:575-582, 2002.

Geddes, L.A. et al., "Criteria for the Selection of Materials for Implanted Electrodes", *Annals of Biomedical Engineering*, vol. 31, pp. 879-890 (2003).

Gepstein et al., "A Novel Method for Nonfluoroscopic Catheter-Based Electroanatomical Mapping of the Heart", *Circulation* 95:1611-1622, 1997.

Gitosusastro et al., "Performance Derivative Calculations and Optimization Process", IEEE Transactions on Magnetics, vol. 25:2834-2839, Jul. 4, 2989.

Hansen: Rank-Deficient and Discrete III-Posed Problems: Numerical Aspects of Linear Inversion, SIAM, Philadelphia, USA, pp. 100-103, 1998.

Huang, Yi-Chih et al., "Development of a Third Generation Intraventricular Impedance Imaging (III) System Evaluation of Hardware Design", *Engineering in Medicine and Biology Society*, Proceedings of the 19th Annual International Conference of the IEEE, Oct. 30-Nov. 2, 1997 vol. 6, (1997).

Jain et al., "Cell Therapy Attenuates Deleterious Ventricular Remodeling and Improved Cardiac Performance After Myocardial Infarction", *Circulation*, 103:1920-1927, 2001.

Jalife, "Rotors and Spiral Waves in Atrial Fibrillation", *Journal of Cardiovascular Electrophysiology*, 14:776-780, 2003.

Jané et al., "Alignment Methods for Averaging of High-Resolution Cardiac Signals: A Comparative Study of Performance", *IEEE Transactions on Biomedical Engineering*, 38(6):571-579, 1991.

Jia et al., "Electrophysiologic Endocardial Mapping from a Noncontact Nonexplandable Catheter: A Validation Study of a Geometry-Based Concept", *Journal of Cardiovascular Electrophysiology*, 11:1238-1251, 2000.

Kikuchi et al., "Targeted Modification of Atrial Electrophysiology by Homogeneous Transmural Atrial Gene Transfer", *Circulation*, 111:264-270, 2005.

Kistler et al., "Validation of Three-Dimensional Cardiac Image Integration: Use of Integrated CT Image into Electroanatomic Mapping System to Perform a Catheter Ablation of Atrial Fibrillation", *Journal of Cardiovascular Electrophysiology*, 17:341-348, 2006.

Kuklik et al., "The reconstruction, from a set of points, and analysis of the interior surface of the heart chamber", Physiol. Meas. 25:617-627, 2004.

Kun, Stevan et al., "Conductance Volumetric Model of an Eccentrically Positioned Catheter Within a Three-Compartment Ellipsoidal Ventricle", U, IEEE Transactions on, Jun. 1993. vol. 40, Issue: 6.

Laciar et al., "Improved Alignment Method for Noisy High-Resolution ECG and Holter Records Using Multiscale Cross-Correlation", *IEEE Transactions on Biomedical Engineering*, 50(3):344-353, 2003.

Liu et al., "Endocardial Potential Mapping from a Noncontact Nonexpandable Catheter: A Feasibility Study", *Annals of Biomedical Engineering*, 26:994-1009, 1998.

Lorensen et al., "Marching Cubes: A High Resolution 3D Surface Construction Algorithm", Computer Graphics 21(4):163-169, Jul. 1987.

Mäkelä et al., "A Review of Cardiac Image Registration Methods", *IEEE Transactions on Medical Imaging*, 21(9):1011-1021, 2002.

Malladi, R. et al., "A Geometric Approach to Segmentation and Analysis of 3D Medical Images", *Mathematical Methods in Biomedical Image Analysis*, Proceedings of the Workshop on Jun. 21-22, 1996, pp. 244-252, (1996).

Mangan, Alan et al., "Partitioning 3D Surface Meshes Using Watershed Segmentation", *IEEE Transactions on Visualization and Computer Graphics*, vol. 05, No. 4, pp. 308-321, (Oct.-Dec. 1999).

Meininger et al., "Initial Experience with a Novel Focused Ultrasound Ablation System for Ring Ablation Outside the Pulmonary Vein", *Journal of Interventional Cardiac Electrophysiology*, 8:141-148, 2003.

Merrill, Daniel R. et al., "Electrical stimulation of excitable tissue: design of efficacious and safe protocols", *Journal of Neuroscience Methods*, vol. 141, pp. 171-198 (2005).

Miller, "Editor's Forum—Application of Registration for Ablation: A Marriage of Technologies", *Journal of Interventional Cardiac Electrophysiology*, 11:87-89, 2004.

Nadarnanee et al., "A New Approach for Catheter Ablation of Atrial Fibrillation: Mapping of the Electrophysiologic Substrate", *Journal of the American College of Cardiology*, 43(11):2044-2053, 2004.

Noseworthy et al., "The Impact of Respiration on Left Atrial and Pulmonary Venous Anatomy: Implications for Image-Guided Intervention", *Heart Rhythm*, 2:1173-1178, 2005.

Pappone et al., "Robotic Magnetic Navigation for Atrial Fibrillation Ablation", *Journal of the American College of Cardiology*, 47(7):1390-1400, 2006.

Paragios, "A Level Set Approach for Shape-Driven Segmentation and Tracking of the Left Ventricle", *IEEE Transactions on Medical Imaging*, 22(6):773-776, 2003.

Persson et al., "A Simple Mesh Generator in MATLAB", *SIAM Review*, 46(2):329-345, 2004.

Persson, "Mesh Generation for Implicit Geometrics", *Massachusetts Institute of Technology—Thesis*, Feb. 5, 2006.

Pham, Dzung et al., "Current Methods in Medical Image Segmentation", *Annu. Rev. Biomed. Eng.*, 02: pp. 315-337, (2000).

Rao et al., "Novel Noncontact Catheter System for Endocardial Electrical and Anatomical Imaging", *Annals of Biomedical Engineering*, 32(4):573-584, 2004.

Reddy et al., "Integration of Cardiac Magnetic Resonance Imaging with Three-Dimensional Electroanatomic Mapping to Guide Left Ventricular Catheter Manipulation—Feasibility in a Porcine Model of Healed Myocardial Infarction", *Journal of the American College of Cardiology*, 44(11):2202-2213, 2004.

Reddy et al., "Use of a Diode Laser Balloon Ablation Catheter to Generate Circumferential Pulmonary Venous Lesions in an Open-Thoracotomy Caprine Model", *PACE*, 27:52-57, 2004.

Sanders et al., "Spectral Analysis Identifies Sites of High-Frequency Activity Maintaining Atrial Fibrillation in Humans", *Circulation*, 112:789-797, 2005.

Sethian, "Level Set Methods and Fast Marching Methods: Evolving Interfaces in Computational Geometry, Fluid Mechanics, Computer Vision and Materials Science", *Department of Mathematics—University of California, Berkeley*, Cambridge University Press, 1999.

Simon et al., "Electroanatomic Mapping of the Right Atrium with a Right Atrial Basket Catheter and Three-Dimensional Intracardiac Echocardiography", *PACE*, 27:318-326, 2004.

Smits et al., "Catheter-Based Intramyocarial Injection of Autologous Skeletal Myoblasts as a Primary Treatment of Ischemic Heart Failure", *Journal of the American College of Cardiology*, 42(12):2063-2069, 2003.

Solomon et al., "Real-Time Cardiac Catheter Navigation on Three-Dimensional CT Images", *Journal of Interventional Cardiac Electrophysiology*, 8:27-36, 2003.

Sra et al., "Registration of Three-Dimensional Left Atrial Computed Tomographic Images with Projection Images Obtained Using Fluoroscopy", *Circulation*, 112:3763-3768, 2005.

(56) References Cited

OTHER PUBLICATIONS

Sra, Jasbir et al, "Registration of 3D Computed Tomographic Images with Interventional Systems: Implications for Catheter Ablation of Atrial Fibrillation", *J Interv Card Electrophysiol.* 16: pp. 141-148, (2006).

Stevenson, "Radiofrequency Catheter Ablation of Ventricular Tachycardia After Myocardial Infarction", *Circulation*, 98:308-314, 1998.

Taccardi et al., "A New Intracavitary Probe for Detecting the Site of the Origin of Ectopic Ventricular Beats During One Cardiac Cycle", *Circulation*, 75(1):272-281, 1987.

Thal et al., "Novel Applications in Catheter Ablation", *Journal of Interventional Cardiac Electrophysiology*, 13:17-21, 2005.

Thiagalingam et al., "Noncontact Mapping of the Left Ventricle: Insights from Validation with Transmural Contact Mapping", *PACE*, 27:570-578, 2008.

Voth, "The Inverse Problem of Electrocardiography: Industrial Solutions and Simulations", BEM and NFSI Conference Proceedings, Minneapolis, MN, May 12-15, 2005, pp. 191-194.

Wittkampf et al., "LocaLisa: New Technique for Real-Time 3-Dimensional Localization of Regular Intracardiac Electrodes", *Circulation*, 99:1312-1317, 1999.

Yezzi, Anthony et al., "A Geometric Snake Model for Segmentation", *IEEE Transactions on Medical Imaging*, vol. 16, No. 2, (Apr. 1997).

\* cited by examiner

IMPEDANCE BASED ANATOMY GENERATION

CROSS-REFERENCE TO RELATED APPLICATIONS

This is a continuation of U.S. application Ser. No. 12/437,794 filed Jun. 8, 2009, now U.S. Pat. No. 8,103,338. All subject matter set forth in the above referenced application is hereby incorporated by reference in its entirety into the present application as if fully set forth herein.

TECHNICAL FIELD

This invention relates to the determination and representation of anatomical information and/or physiological information relating to a heart using, e.g., a non-contact catheter.

BACKGROUND

Use of minimally invasive procedures, such as catheter ablation, to treat a variety of heart conditions, such as supraventricular and ventricular arrhythmias, is becoming increasingly more prevalent. Such procedures involve the mapping of electrical activity in the heart (e.g., based on cardiac signals), such as at various locations on the endocardium surface ("cardiac mapping"), to identify the site of origin of the arrhythmia followed by a targeted ablation of the site. To perform such cardiac mapping a catheter with one or more electrodes can be inserted into the patient's heart chamber.

Conventional 3D mapping techniques include contact mapping and non-contact mapping. In contact mapping techniques one or more catheters are advanced into the heart. Physiological signals resulting from the electrical activity of the heart are acquired with one or more electrodes located at the catheter distal tip after determining that the tip is in stable and steady contact with the endocardium surface of a particular heart chamber. Location and electrical activity is usually measured sequentially on a point-by-point basis at about 50 to 200 points on the internal surface of the heart to construct an electro-anatomical depiction of the heart. The generated map may then serve as the basis for deciding on a therapeutic course of action, for example, tissue ablation, to alter the propagation of the heart's electrical activity and to restore normal heart rhythm. On the other hand, in non-contact-based mapping systems a multiple electrodes catheter is percutaneously placed in the heart chamber of interest. Once in the chamber, the catheter is deployed to assume a 3D shape. Using the signals detected by the non-contact electrodes and information on chamber anatomy and relative electrode location, the system provides physiological information regarding the endocardium of the heart chamber.

SUMMARY

In some aspects, a method includes inserting a catheter into a heart, the catheter comprising three or more electrodes. The method also includes moving the catheter to each of multiple, different positions in the heart. The method also includes for each of the different catheter positions, causing current to flow between at least some of the electrodes and in response to current flow, measuring an electrical signal at each of one or more of the electrodes. The method also includes determining anatomical information about the heart based on positions of the catheter electrodes and the measured signals at the different catheter positions.

Embodiments can include one or more of the following.

The determination of the anatomical information accounts for a change in conductivity at the cardiac chamber boundary. The determination accounts for a first conductivity inside the cardiac chamber boundary and a second conductivity outside the cardiac chamber boundary. Determining the anatomical information can include determining the anatomical information based at least in part on impedance information generated based on the measured signals at the different catheter positions. The impedance information is based on a conductivity contrast between blood and surrounding tissue.

The anatomical information can include a representation of at least a portion of a boundary of the heart.

Determining the anatomical information can include detecting a boundary of the heart. Determining the anatomical information can include, for each of the different catheter positions, determining a surface based on the measured signals, the surface representing a surface at which the conductivity changes. The surface can be a closed and parameterized surface around at least a portion of the catheter. The surface can be an ellipsoid. The surface can be a curvilinear surface. The surface can provide a boundary between a region represented by a first conductivity inside the surface and a region represented by a second conductivity outside the surface, the first conductivity being different from the second conductivity.

Determining the anatomical information can include, for each of the determined surfaces selecting one or more regions of the surface corresponding to a boundary of a portion of the heart.

Selecting the one or more regions can include selecting the one or more regions based at least in part on a distance between a portion of the surface and the catheter. Selecting the one or more regions can include selecting the one or more regions based at least in part, on a magnitude, of a distortion field, the distortion field being based at least in part on a difference between, a field calculated based on the measurements and a field in a homogonous medium. Selecting the one or more regions can include selecting the one or more regions based at least in part on an error calculation in an optimization used to generate the surface. Determining the anatomical information can include joining the regions of the determined surfaces corresponding to an expected chamber boundary to generate the anatomical information. Joining the regions can include using a meshing algorithm.

The method can also include using the multiple electrodes on the catheter to measure cardiac signals at the catheter electrodes in response to electrical activity in the heart.

The method can also include determining physiological information at multiple locations of the boundary of the heart based on the determined positions of the catheter electrodes and the measured cardiac signals at the different catheter positions.

The method, can also include using one or more electrodes on the catheter for delivering ablation energy for ablating tissue.

Determining the anatomical information based on the measured signals from the one or more electrodes can include distinguishing electrical signals indicative of cardiac electrical activity from those responsive to the injected current.

The method can also include displaying at least a portion of the anatomical information. Displaying at least a portion of the anatomical information can include displaying at least a portion of the boundary of the heart.

In some additional aspects, a method can include inserting a catheter into a heart, the catheter comprising multiple, spatially distributed electrodes including multiple sets of electrodes each set comprising at least two electrodes. The method can also include for each of the multiple different sets of electrodes, causing current to flow between at least some of the electrodes and in response to current flow, measuring an electrical signal at each of one or more measuring electrodes. The method can also include determining anatomical information based on the measured signals.

Embodiments can include one or more of the following.

The determination of the anatomical information can account for a change in conductivity at the cardiac chamber boundary.

The determination can account for a first conductivity inside the cardiac chamber boundary and a second conductivity outside the cardiac chamber boundary.

Determining the anatomical information can include determining the anatomical information based at least in part on impedance information generated based on the measured signals. The impedance information can be based on a conductivity contrast between blood and surrounding tissue. The anatomical information can include a representation of at least a portion of a boundary of the heart.

Determining the anatomical information can include detecting a boundary of the heart. Determining the anatomical information can include determining a surface based on the measured signals, the surface representing a surface at which the conductivity value changes. The surface can be a closed and parameterized surface around at least a portion of the catheter. The surface can be an ellipsoid. The surface can be a curvilinear surface. The surface can provide a boundary between a region represented by a first conductivity inside the surface and a region represented by a second conductivity outside the surface, the first conductivity being different from the second conductivity.

Determining the anatomical information can include for each of the determined surfaces selecting one or more regions of the surface, corresponding to an expected boundary of the heart. Selecting the one or more regions can include selecting the one or more regions based at least in part on a distance between a portion of the surface and the catheter. Selecting the one or more regions can include selecting the one or more regions based at least in part on a magnitude, of a distortion field, the distortion field being based at least in part on a difference between a field calculated based on the measurements and a field in a homogonous medium. Selecting the one or more regions can include selecting the one or more regions based at least in part on an error calculation in an optimization used to generate the surface.

Determining the anatomical information can include joining the regions of the determined surfaces corresponding to an expected chamber boundary to generate the anatomical information. Joining the regions can include using a meshing algorithm.

The method can also include using the multiple electrodes on the catheter to measure cardiac signals at the catheter electrodes in response to electrical activity in the heart.

The method can also include determining physiological information at multiple locations of the boundary of the heart based on positions of the catheter electrodes and the measured cardiac signals. The method can also include using one or more electrodes on the catheter for delivering ablation energy for ablating tissue.

Determining the anatomical information based on the measured signals from the one or more electrodes can include distinguishing electrical signals indicative of cardiac electrical activity from those responsive to the injected current.

The method can also include displaying at least a portion of the anatomical information.

In some aspects, a method includes inserting a catheter into a heart, the catheter comprising three or more electrodes. The method also includes causing current to flow between at least some of the electrodes and in response to current flow, measuring an electrical signal at each of one or more of the electrodes. The method also includes determining a boundary of at least a portion of the heart based on the measured electrical signals. The method also includes displaying a portion of less than the entire boundary of the heart.

Embodiments can include one or more of the following.

The method can also include measuring cardiac signals at the catheter electrodes in response to electrical activity in the heart and determining physiological information at multiple locations of the boundary of the heart based the measured cardiac signals.

The method can also include displaying the physiological information at multiple locations of the boundary of the heart.

The method can also include displaying the physiological information at multiple locations of the boundary of the heart for only a determined valid area. Displaying the boundary can include displaying the boundary for a portion of less than all of the heart.

The determination of the boundary can accounts for a change in conductivity at the cardiac chamber boundary. The determination can account for a first conductivity inside the cardiac chamber boundary and a second conductivity outside the cardiac chamber boundary.

Determining the boundary can include determining the anatomical information based at least in part on impedance information generated based on the measured signals. The impedance information can be based on a conductivity contrast between blood and surrounding tissue.

Determining the boundary can include determining a surface based on the measured signals, the surface representing a surface at which the conductivity value changes. The surface can be a closed and parameterized surface around at least a portion of the catheter. The surface can provide a boundary between a region represented by a first conductivity inside the surface and a region represented by a second conductivity outside the surface, the first conductivity being different from the second conductivity.

Determining the anatomical information can include for each of the determined surfaces selecting one or more regions of the surface corresponding to an expected boundary of the heart. Selecting the one or more regions can include selecting the one or more regions based at least in part on a distance between a portion of the surface and the catheter. Selecting the one or more regions can include selecting the one or more regions based at least in part on a magnitude of a distortion field, the distortion field being based at least in part on a difference between a field calculated based on the measurements and a field in a homogonous medium. Selecting the one or more regions can include selecting the one or more regions based at least in part on an error calculation in an optimization used to generate the surface.

Determining the anatomical information can include joining the regions of the determined surfaces corresponding to an expected chamber boundary to generate the anatomical information.

The method can also include determining a valid area of the boundary and using a visual indicia to indicate the determined valid area of the boundary.

Displaying the portion of less than the entire boundary of the heart can include using a visual indicia to indicate a valid area of the boundary.

The method can also include determining a valid area of the boundary. Displaying the portion of less than the entire boundary of the heart comprises using a visual indicia to indicate the determined valid area of the boundary.

In some aspects, a system includes a catheter comprising one or more electrodes configured to inject a current and to measure electrical signals in response to the injected current. The system also includes a device configured to determine a position of the catheter electrodes. The system also includes a processing unit configured to determine anatomical information about the heart based on positions of the catheter electrodes and measured electrical signals at different catheter positions.

Embodiments can include one or more of the following.

The processing unit can be configured to account for a change in conductivity at a cardiac chamber boundary in the determination of the anatomical information.

The processing unit can be configured to account for a first conductivity inside the cardiac chamber boundary and a second conductivity outside the cardiac chamber boundary.

The processing unit can be configured to determine the anatomical information based at least in part on impedance information. The impedance information can be based on a conductivity contrast between blood and surrounding tissue.

The anatomical information can include a representation of at least a portion of a boundary of the heart.

The processing unit can be configured to determine the anatomical information by determining a surface based on the measured signals, the surface representing a surface at which the conductivity changes.

The processing unit can be configured to, for each of the determined surfaces, select one or more regions of the surface corresponding to a boundary of a portion of the heart.

The processing unit can be configured to select the one or more regions based at least in part on a distance between a portion of the surface and the electrodes.

The processing unit can be configured to select the one or more regions based at least in part on a magnitude of a distortion field, the distortion field being based at least in part on a difference between a field calculated based on the measurements and a field in a homogonous medium.

The processing unit can be configured to select the one or more regions based at least in part on an error calculation in an optimization used to generate the surface.

The processing unit can be configured to join the regions of the determined surfaces corresponding to an expected chamber boundary to generate the anatomical information.

The multiple electrodes can be further configured to measure cardiac signals in response to electrical activity in the heart.

The processing unit can be configured to determine physiological information at multiple locations of the boundary of the heart based on positions of the catheter electrodes and measured cardiac signals.

In some aspects, a system includes a catheter comprising multiple, spatially distributed electrodes including multiple sets of electrodes each set comprising at least two electrodes, the electrodes being configured to inject a current and to measure electrical signals in response to the injected current. The system also includes a processing unit configured to determine anatomical information about the heart based on the measured signals.

Embodiments can include one or more of the following.

The processing unit can be configured to account for a change in conductivity at the cardiac chamber boundary in the determination of the anatomical information.

The processing unit can be configured to account for a first conductivity inside the cardiac chamber boundary and a second conductivity outside the cardiac chamber boundary.

The processing unit can be configured to determine the anatomical information based at least in part on impedance information generated based on the measured signals at the different catheter positions.

The impedance information can be based on a conductivity contrast between blood and surrounding tissue.

The anatomical information can include a representation of at least a portion of a boundary of the heart.

The processing unit can be configured to determine the anatomical information by determining a surface based on the measured signals, the surface representing a surface at which the conductivity changes.

The processing unit can be configured to for each of the determined surfaces, select one or more regions of the surface corresponding to a boundary of a portion of the heart.

The processing unit can be configured to select the one or more regions based at least in part on a distance between a portion of the surface and the catheter.

The processing unit can be configured to select the one or more regions based at least in part on a magnitude of a distortion field, the distortion field being based at least in part on a difference between a field calculated based on the measurements and a field in a homogonous medium.

The processing unit can be configured to select the one or more regions based at least in part on an error calculation in ah optimization used to generate the surface.

The processing unit can be configured to join the regions of the determined surfaces corresponding to an expected chamber boundary to generate the anatomical information.

The electrodes on the catheter can be further configured to measure cardiac signals in response to electrical activity in the heart.

The processing unit can be configured to determine physiological information at multiple locations of the boundary of the heart based on the determined positions of the catheter electrodes and the measured cardiac signals.

In some aspects, a system includes a catheter that includes two or more electrodes configured to inject a current and to measure electrical signals. The system also includes a processing unit configured to determine a boundary of at least a portion of the heart based on the measured electrical signals and a display device configured to display a portion of less than the entire boundary of the heart.

Embodiments can include one or more of the following.

The two or more electrodes can be further configured to measure cardiac signals in response to electrical activity in the heart and the processing unit can be further configured to determine physiological information at multiple locations of the boundary of the heart based the measured cardiac signals.

The display device can be further configured to display the physiological information at multiple locations of the boundary of the heart.

The system can be configured to display the physiological information at multiple locations of the boundary of the heart for only the determined valid area.

The processing unit can be configured to account for a change in conductivity at the cardiac chamber boundary in the determination of the boundary.

The processing unit can be configured to account for a first conductivity inside the cardiac chamber boundary and a second conductivity outside the cardiac chamber boundary.

The processing unit can be configured to determine the boundary based at least in part on impedance information generated based on the measured signals at the different catheter positions.

The impedance information can be based on a conductivity contrast between blood and surrounding tissue.

The processing unit can be configured to determine the boundary by determining a surface based on the measured signals, the surface representing a surface at which the conductivity changes.

The processing unit can be configured to for each of the determined surfaces select one or more regions of the surface corresponding; to a boundary of a portion of the heart.

The processing unit can be configured to select the one or more regions based at least in part on a distance between a portion of the surface and the catheter.

The processing unit can be configured to select the one or more regions based at least in part on a magnitude of a distortion field, the distortion field being based at least in part on a difference between a field calculated based on the measurements and a field in a homogonous medium.

The processing unit can be configured to select the one or more regions based at least in part on an error calculation in an optimization used to generate the surface.

The processing unit can be configured to join the regions of the determined surfaces corresponding to an expected chamber boundary to generate the anatomical information.

The two or more electrodes can be further configured to measure cardiac signals in response to electrical activity in the heart.

The processing unit can be configured to determine physiological information at multiple locations of the boundary of the heart based on the determined positions of the catheter electrodes and the measured cardiac signals.

Embodiments of the system may also include devices, software, components, and/or systems to perform any features described above.

Embodiments of the methods and systems generally disclosed herein can be applied to determining the position of any object within an organ in a patient's body such as the patient's heart, lungs, brain, or liver.

As used herein, the "position" of an object means information about one or more of the 6 degrees of freedom that completely define the location and orientation of a three-dimensional object in a three-dimensional coordinate system. For example, the position of the object can include: three independent values indicative of the coordinates of a point of the object in a Cartesian coordinate system and three independent values indicative of the angles for the orientation of the object about each of the Cartesian axes; or any subset of such values.

As used herein, "heart cavity" means the heart and surrounding tissue.

As used herein, the "anatomical information" means information about an anatomy of an organ, information about a boundary of an organ, and/or information about an anatomy for ablation.

Unless otherwise defined, all technical and scientific terms used herein have the same meaning as commonly understood by one of ordinary skill in the art to which this invention belongs. In case of conflict with documents incorporated herein by reference, the present document controls.

The details of one or more embodiments of the invention are set forth in the accompanying drawings and the description below. Other features, objects, and advantages of the invention will be apparent from the description and drawings, and from the claims.

DESCRIPTION OF THE DRAWINGS

Like reference symbols in the various drawings indicate like elements.

DETAILED DESCRIPTION

Embodiments disclosed herein include a method and system for generating patient specific anatomical information such as cardiac anatomy. The patient specific cardiac anatomy can be used, for example, during the generation of an electroanatomical map (EAM) of heart tissue which can be used to identify the site of origin of an arrhythmia followed by a targeted ablation of the site. While patient specific anatomy is a necessary component in the generation of an EAM for the catheter ablation treatment of arrhythmia, accurate representation of cardiac anatomy is useful for other medical applications such as congestive heart failure, injection of biologies into the heart and scar tissue, anatomical guidance of biopsies, minimally invasive valve repair and replacement, and the like.

Figure 1:
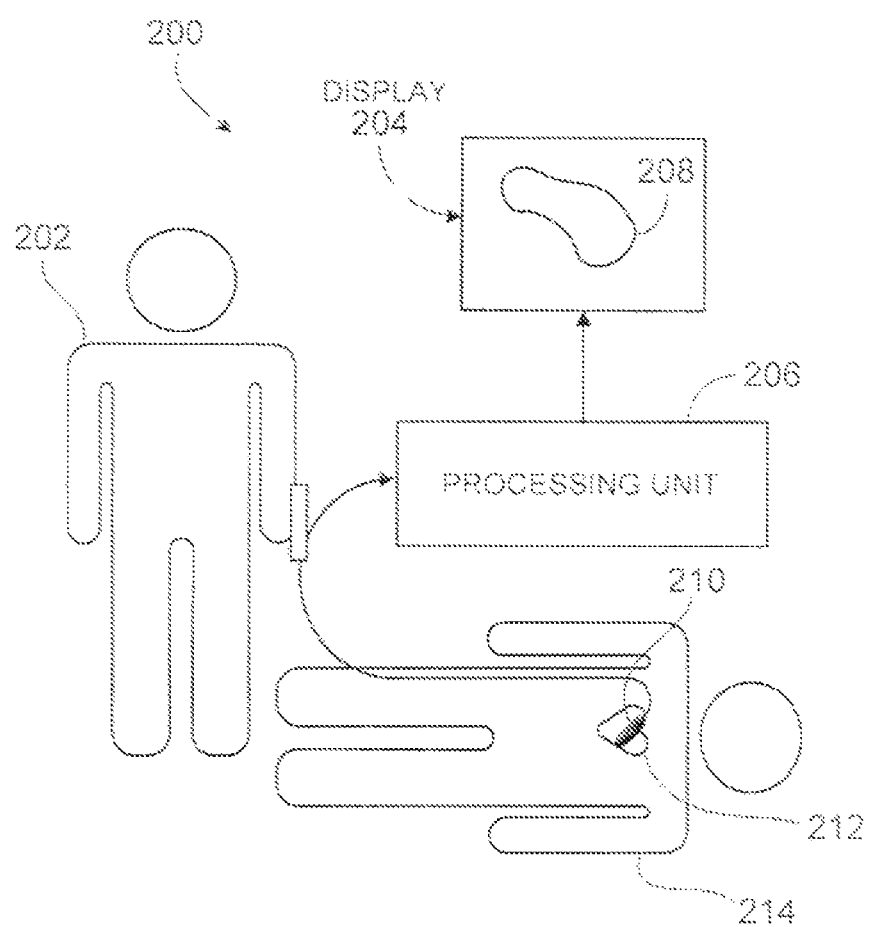
FIG. 1 is an exemplary schematic diagram of an arrangement for positioning electrodes in a patient's heart.

Embodiments disclosed herein include methods and systems for generating anatomical information including patient specific anatomy by deriving impedance based information from a tracked multi-electrode array (MEA) catheter. FIG. 1 shows a schematic diagram of an exemplary embodiment of a anatomy generation system 200. The system 200 includes a moveable catheter 210 having multiple spatially distributed electrodes (described below). During the anatomy generation process, a physician or medical professional 202 inserts the catheter 210 into a chamber of interest (e.g., the heart 212) of a patient 214. The catheter 210 is displaced to one or multiple locations within the chamber of interest (e.g., the heart 212). In some embodiments, the distal end of the catheter 210 is fitted with multiple electrodes spread somewhat uniformly over the catheter (e.g., as described in more detail below). The catheter 210 includes both current injection electrodes (CIE) and potential measuring electrodes (PME). In the example of anatomy generation for the heart chamber, due to the conductivity contrast between blood and the myocardium and surrounding tissue, the measurements collected by the catheter 210 can be analyzed to detect chamber boundary in the vicinity of the catheter 210. In order to reconstruct the chamber anatomy, system 200 includes a processing unit 206 which performs operations pertaining to anatomy determination based on a location of the catheter 210 (e.g., a location provided by a tracking system) and the measurements from the electrodes on the catheter 210. As the tracked catheter 210 is moved inside the chamber, a partial or complete representation of the chamber anatomy is constructed. For example, a representation of the boundary of the chamber can be constructed. The chamber anatomy 208 can be displayed on a display device 204 which is connected to the processing unit 206. In addition, embodiments disclosed herein include methods and systems for generating an EAM using the generated anatomy.

In addition, embodiments disclosed herein include methods and systems for generating partial chamber boundary EAM. The partial chamber boundary EAM provides physiological information about a portion (e.g., a portion of less than the entire) of a chamber such as the heart. Partial chamber boundary EAM can be useful to quickly obtain an EAM in a known area of interest. The construction of partial EAM is enabled by the ability to reconstruct the anatomy of a part of the chamber coupled with knowledge of valid and invalid zones obtained by using the disclosed impedance scheme.

As described herein, due to the conductivity contrast between blood and the myocardium and surrounding tissue, measurements collected by catheter 210 located inside the heart 212 of a patient 214 can be analyzed to detect a chamber boundary in the vicinity of the catheter 212. These measurements can be used to generate anatomical information representing the anatomy of the heart. Other exemplary methods for generating an anatomy of the heart (or other organ) include point collection, ultrasound, rotational angiography, computed tomography (CT) and magnetic resonance (MR). In general, point collection is a method in which a tracked catheter is moved inside the heart and numerous catheter locations are collected. Overtime the outline of the heart is traced based on the collection of points. Exemplary drawbacks of point collection for generation of an anatomy can include that the process is time consuming and can suffer from limited accuracy and uncertainty. Ultrasound is a method in which a tracked intra cardiac ultrasound/echo catheter is moved inside the heart, the 2D images collected with the catheter are segmented to identify chamber boundary and combined using the 3D tracking data. Exemplary drawbacks of ultrasound for generation of an anatomy can include that the process can be time consuming, segmentation is manual, and a proprietary ultrasound catheter must be introduced into the organ solely for determining anatomy. Rotational Angiography is a method in which a contrast agent is injected into chamber of interest and a fluoroscopy c-arm is rotated to obtain volumetric representation. Segmentation is used to detect endocardial boundary. Exemplary drawbacks of rotational angiography can include that its use can lengthen procedure time, may suffer from limited accuracy, it can be difficult to image all chambers, and/or excessive injection of contrast may be toxic. When CT & MR are used, a volumetric chamber representation is acquired ahead of procedure, volume segmentation provides cardiac chamber of interest, and registration to tracking system is performed during procedure. Exemplary drawbacks of CT and MR can include that the anatomy is generated prior to the procedure which may lead to inaccuracy in anatomy at the time of the procedure, the process often requires use of contrast agent, and/or not all chambers can easily be imaged.

It is believed that generating the anatomy based on measurements collected by a catheter located inside the heart of a patient and calculations based on the conductivity contrast between blood and the myocardium and surrounding tissue (e.g., as described herein) can provide one or more of the following advantages. The generation of the anatomy can be relatively fast, since a large area of the anatomy can be acquired in each heartbeat. In another example, the anatomy information is acquired (and may be re-acquired) during the procedure as opposed to being acquired prior to the procedure. In another example, these methods can provide the advantage enabling the same catheter to be used for anatomy generation, electrical reconstruction, and/or tracking.

In some embodiments, a patient specific anatomy is generated using impedance based information from a tracked multi-electrode array (MEA) catheter. The system includes an MEA catheter that provides mechanical support for an array of current injecting electrodes (CIE) and potential measuring electrodes (PME). For example, the catheter may be configured with multiple electrodes and used for cardiac mapping, such as described in commonly owned patent application Ser. No. 11/451,898, entitled "NON-CONTACT CARDIAC MAPPING, INCLUDING MOVING CATHETER AND MULTI-BEAT INTEGRATION" and filed Jun. 13, 2006, application Ser. No. 11/451,908, entitled "NON-CONTACT CARDIAC MAPPING, INCLUDING PRE-PROCESSING" and filed Jun. 13, 2006, application Ser. No. 11/451,871 entitled "NON-CONTACT CARDIAC MAPPING, INCLUDING RESOLUTION MAP" and filed Jun. 13, 2006, and application Ser. No. 11/672,562 entitled "IMPEDANCE REGISTRATION AND CATHETER TRACKING" and filed Feb. 8, 2007, the contents of each of which are incorporated herein by reference. The system also includes electronics for driving current and measuring potential, a tracking system that provides 3D location of catheter electrodes, and a computer with appropriate software algorithm to collect data and process the data in order to construct a 3D representation of the chamber anatomy.

The MEA Catheter

The MEA catheter can be normally introduced through a femoral vein or artery and advanced into the heart through the vascular system. The MEA catheter has a multitude of electrodes that deploy into a three dimensional shape. For example, the MEA catheter may have 64 electrodes and deploy into a relatively spherical shape with a diameter of about 2 cm. The MEA catheter may be used to collect cardiac signals, tracking signals, as well as to generate and collect the signals necessary determining anatomical information such as the boundary of an organ such as the heart.

To generate the excitation pattern necessary for anatomy construction, a sequence of linearly independent current injection patterns are generated by utilizing current injecting electrodes ("CIE") on the catheter. Simultaneously potential measurement is performed on potential measuring electrodes ("PME"), also mounted on the catheter. It should be noted that PME and CIE may be one and the same.

Figure 2A:
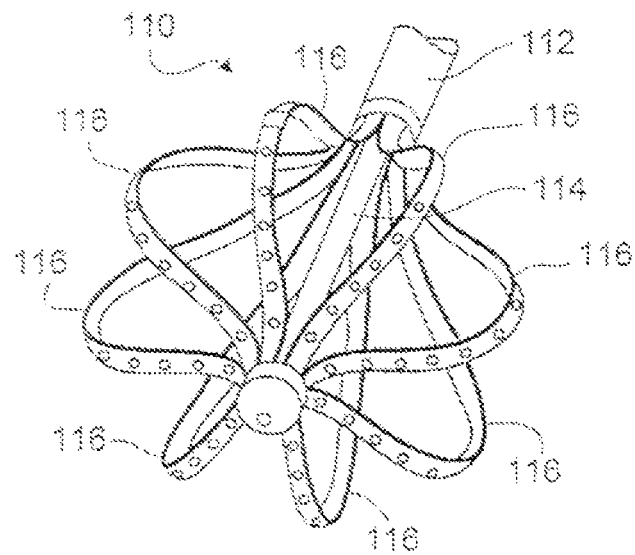
FIGS. 2a-2c show perspective, end, and side views, respectively, of a deployed catheter with multiple current injection electrodes (CIE) and multiple potential measuring electrodes (PME).
Figure 2B:
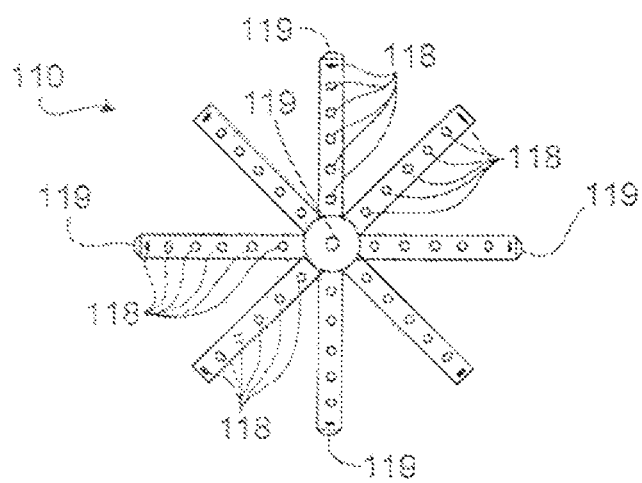
Figure 2C:
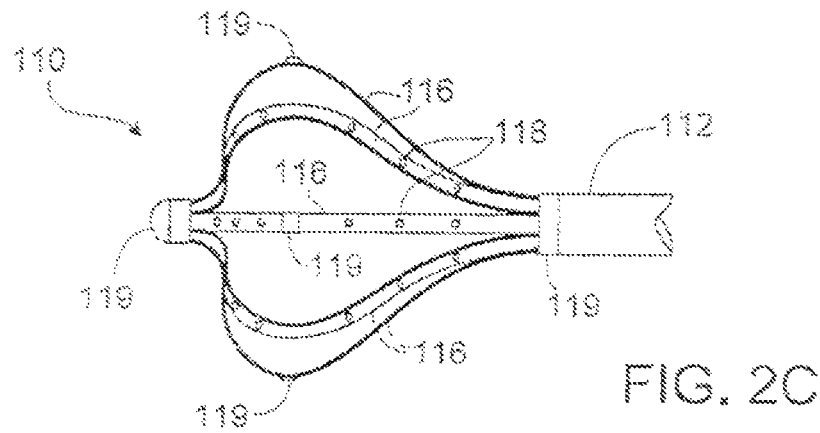

FIGS. 2a-c show different views for one embodiment of the catheter 110, which includes a base sleeve 112, a central retractable inner member 114, and multiple splines 116 connected to base sleeve 112 at one end and inner member 114 at the other end. When inner member 114 is in an extended configuration (not shown), splines 116 are pulled tight to the inner member so that catheter 110 has a narrow profile for guiding it through blood vessels. When inner member 114 is retracted (as shown in FIGS. 2a-b), splines 116 are deployed and pushed into an outward "olive" shaped configuration for use in the heart cavity. As explained in more detail below, the splines 116 each carry electrodes, so when the inner member is in the retracted configuration, the electrode are deployed in the sense that they are distributed over a greater volume.

A number (>6) of current injecting electrodes (CIE) are mounted on catheter 110. For example, 3 orthogonal CIE pairs may be mounted on the catheter.

The CIE are designated 119, while electrodes 118 are used as potential measuring electrodes (PME). The purpose of the CIEs is to inject current into the heart cavity. For example, each CIE pair can define a source and sink electrode, respectively, for injecting current into the heart cavity.

It should be noted that any low impedance electrode can be used for current injection and in a case where many or all electrodes are capable of injecting current the designation of such electrodes as CIE on the catheter only indicates that these electrodes are actually being used for current injection. It should be further appreciated that other configuration sets of CIE are possible as long as these configurations are known and can be accounted for. Examples of such configurations could be quadruples involving 4 CIE, or even a non-symmetrical configuration involving 3 CIE in known positions on the catheter. For simplicity the method of using electrode pairs will be explained, but the same method can be applied using other configurations.

Figure 3B:
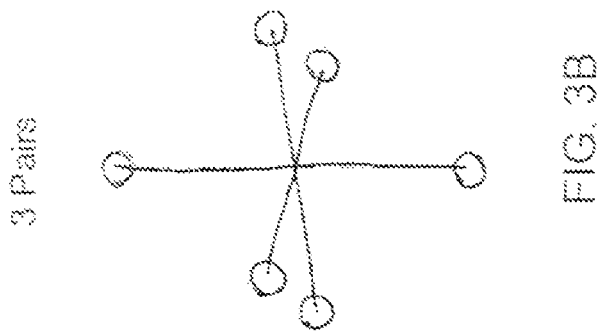
FIGS. 3A and 3B are schematic diagrams of two current injection electrodes (CIE) pair constellations.
Figure 3A:
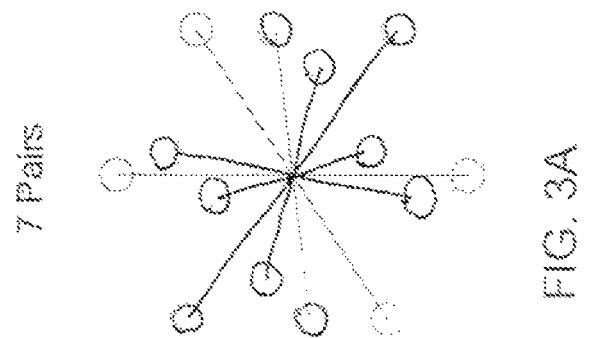

It should be appreciated that configurations other than orthogonal pairs may be used for either method, and that more than 2 CIE may participate in current injection at a given time. FIGS. 3A and 3B show two different CIE pair constellations. FIG. 3B shows the 3 pair constellation described above while FIG. 3A shows 7 pairs. The 7 pairs are the same 3, plus 4 additional diagonal pairs.

Electronics

The MEA catheter is connected to electronics hardware capable of driving the necessary current and detecting both signals originating from, the heart as well as those used for anatomy construction. There is a need to distinguish between the two signals in order to separate the signal being used for the anatomy determination from the cardiac signal. The CIE are therefore coupled to electronics injecting the current at a frequency higher than cardiac activation (cardiac activation <2 kHz, CIE>4 kHz, e.g. 5 kHz) such that the two types of signals can be easily distinguished using frequency analysis. It should be noted that other methods for distinguishing between the CIE signal and the cardiac activation signal can be used, such as injecting a spread-spectrum signal having a low energy level in the frequency range of the cardiac activation signal, and detecting this spread-spectrum signal in the signal collected by the all PME.

A multitude of separate known configurations of CIE need to inject current in order to interrogate the medium. There is a need to determine the source of the injected signal and to trace it to a specific CIE configuration. For example, 3 pairs of CIE can inject the current sequentially, one pair at a time, so that it is possible to trace the source of the measured PME signals to a specific pair. This is called time division multiplexing. In the case of time division multiplexing, CIE are activated in sequence such that at one point in time one pair is activated and at the next point in time another pair is activated. The switching between pairs may occur every cycle (e.g., ⅕ kHz=200 µs) or every few cycles (e.g., 20 cycles, 20×200 µs=4 mS). It should be noted that frequency or code division (spread spectrum) multiplexing, rather than time division may be used to separate the signals emanating from different CIE pairs. In the case of frequency multiplexing all CIE pairs may inject the current at the same time, but each pair uses a different carrier frequency. The signal collected at the PME is filtered according to the frequency, and the signal measured in each frequency is then associated with the appropriate originating pair.

The amount of current injected needs to be large enough to provide a reasonable signal to noise ratio, while also small enough not to stimulate cardiac tissue. A current level of 50 µA at 5 kHz is believed to be appropriate.

Tracking System

In order to combine information collected from multiple catheter locations, the MEA electrode locations are tracked relative to the cardiac chamber in three dimensional space. This task is accomplished by a tracking subsystem. Such subsystems have been shown previously and may include any of a magnetic, impedance, x-ray and ultrasound subsystems. For example, the tracking system can be a tracking system such as described in commonly owned patent application Ser. No. 12/061,297, entitled "Intracardiac Tracking System" and filed Apr. 2, 2008, the contents of which is incorporated herein by reference.

In case of impedance tracking the tracking signals may be multiplexed onto the same medium either by a time division multiplexing scheme where time slots are added specifically for tracking, or using frequency division multiplexing by modulating the tracking signals on a different frequency. In some cases the same CIE pairs may be used simultaneously for tracking and anatomy construction thereby not adding time slots beyond those necessary for tracking.

Data Processing

The system includes software for processing data collected by the MEA catheter and tracking system to generate anatomical information such as a chamber anatomy or representation of a boundary of the chamber.

Referring to FIGS. 4A-4D, a process for generating anatomical information such as a chamber anatomy is shown. In general, when the catheter is in the heart, the signals measured by the PME are different from that of the homogenous case, that is, when the entire domain is filled with blood. These differences carry the particular information about the inhomogeneous distribution of the material property due to the anatomical features around the catheter. This impedance characterization does not gather reliable information from great distances due to the smoothing effect of the Laplace's equation which governs potential distribution in the medium: the injected current will not diffuse substantially into regions far from the Catheter. As such, the system generates information about local anatomical features by detecting and recognizing differences based on the inhomogeneous distribution. In order to reconstruct the entire chamber anatomy, the catheter is moved around the chamber's interior and the impedance characterization is repeated in several locations. Finally, the collected local anatomical information belonging to the different locations, is merged to form the anatomy of the entire chamber.

Figure 4A:
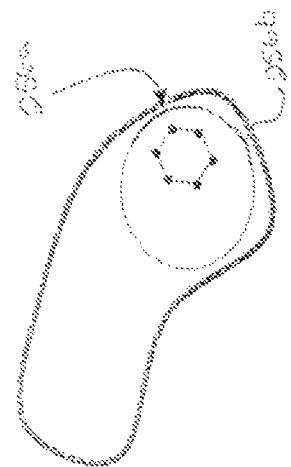
FIGS. 4A-4E are schematic diagrams of a process for generating anatomical information including a reconstructed anatomy.
Figure 4B:
Figure 4C:
Figure 4D:
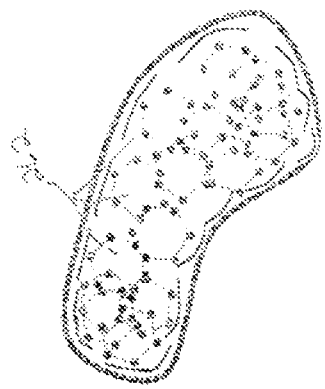
Figure 4E:

FIG. 4A shows a schematic description of true chamber boundary 250, a single catheter 254 and a local parameterized surface 252 reconstructed from the single catheter position. The local parameterized surface 252 is generated based on measurements collected by the PME on catheter 254. As described above, impedance characterization does not gather information from great distances and therefore the local parameterized surface 254 provides only a portion of the chamber anatomy. More particularly, since a single catheter location cannot detect the entire chamber anatomy, the local parameterized surface 242 is a surface that provides a best fit to PME measurements at a particular catheter location (e.g., as described in more detail below). As shown in FIG. 4B, after the local surface 252 is generated for a particular catheter location, the system detects and marks regions of the local parameterized surface 252 that are valid. Valid regions of the local surface 252 are region(s) that are expected to lie on the true chamber boundary 250. These regions are detected and marked as valid patches (e.g., patches 256a and 256b). As shown in FIG. 4C, the catheter 254 is then moved to another location (e.g., moved from location 258a to location 258b) and the process of construction of local anatomy and detection of valid patches is repeated. As shown in FIG. 4C, the system detects another valid patch 256c based on the information collected by catheter 254 at location 258b. As shown in FIG. 4D, to reconstruct the entire chamber anatomy or portion of interest (e.g., a portion of the chamber anatomy, but not the entire chamber anatomy), the catheter is moved to multiple locations, using the tracking system for position information in each location. At each location, the system detects additional valid patches corresponding to additional region(s) that are expected to lie on the true chamber boundary 250. As shown in FIG. 4E, once the catheter has been moved around the entire chamber or the portion of interest, the chamber boundary 260 is reconstructed by connecting the valid patches. In some embodiments, the valid patches can be connected using a surface meshing algorithm such as the algorithm described in U.S. Pat. No. 6,226,542, the contents of which are hereby incorporated by reference.

Cardiac contraction changes the anatomy of the chamber. For that reason, in some embodiments, the anatomy generation is gated according to the cardiac cycle. Gating information can be obtained from electrical measurements of the cardiac cycle (e.g., by the use of surface ECG or intracardiac signal from a stable location) and triggering on a constant marker in the cardiac phase (e.g., using an R-wave detection algorithm, a threshold criterion, a maximum criterion or correlation to a template). Another option is to use a measurement that is affected directly by the mechanical movement of the heart, such as the measurement of the impedance between CIE, and triggering on a constant marker in the cycle. Once a trigger is determined, the cardiac cycle is divided into m slices (e.g., m=10), and the mentioned process is repeated for each slice separately. Alternatively, a particular slice of interest may be chosen (e.g., end diastole) and other data is not collected and/or is discarded. It is also important to note that all CIE sets may be scanned quickly enough (e.g., 4 mS) such that it can be assumed that the heart did not move substantially in that period.

Though sinusoidal signals are used to modulate the signal such that it does not interfere with cardiac signal, the frequency is relatively low, and so the validity of the quasi-static approximation via the Laplace's equation remains intact:

$$\nabla \cdot (\sigma + j\omega\epsilon)\nabla\phi = 0 \quad \text{(Eq. 1)}$$

Where $\phi$ describes the electric potential field, $\sigma$ is the conductivity, $\epsilon$ is the permittivity and $\omega$ is the angular frequency.

Inverse Problem Approach

The anatomical information provides a three dimensional distribution of the electrical conductivity of the surrounding media. The goal of the algorithm is to find the location and orientation of the internal boundary of the heart chamber, that is, to find the boundary where the conductivity value changes from the value associated with blood. For example, on average the conductivity contrast between blood $\sigma_b$ and surrounding tissue $\sigma_t$ is $\sigma^b/\sigma_t = 2.5$. Theoretically, an impedance tomography technique, which is able to provide the distribution of the conductivity surrounding the medium, could be used to detect the anatomical features. However, due to the smoothing effect of current's distribution in material as governed by Laplace's equation, impedance tomography techniques provide blurry representation of the medium and therefore are not ideal for the anatomy reconstruction process. For example the impedance tomography techniques often employ a Tikhonov regularization operator as part of the inverse solution for conductivity. This type of regularization promotes limited change in electrical conductivity over a neighborhood and therefore contributes to the blurriness of the final representation. In general, regularization techniques in inverse problems usually introduce extra equations or terms, which express a priory expectation about the solution and at the same time mathematically convert the underlying equation system from underdetermined to over determined, thereby making it solvable. In other words, regularization techniques are needed in inverse problems to handle the overly high number of unknown degrees of freedom, which is used to represent the conductivity distribution.

Figure 5:
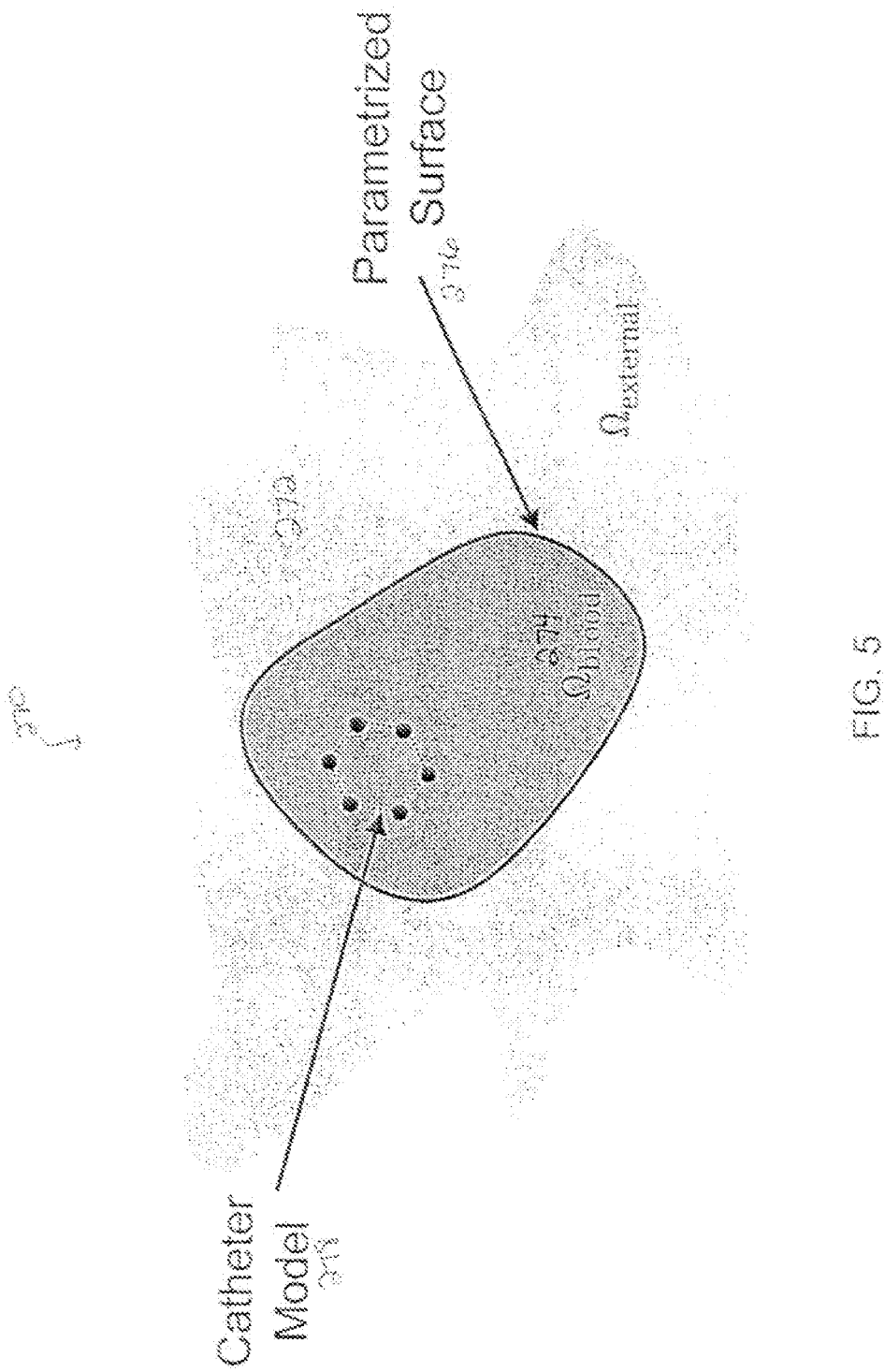
FIG. 5 is a schematic diagram of a model for determining a parameterized surface.

Instead of using an overly high number of degrees of freedom, in some embodiments the abrupt conductivity distribution is represented in a way that uses only a few parameters. For example, as shown in FIG. 5, this can be achieved by an explicit representation of a closed and parameterized local surface 276 around the catheter 278. This representation divides the 3D space into two regions 274 and 272. The region 274 in which the catheter 278 is located is associated with the conductivity of blood ($\Omega_{blood}$) while the outside region 272 is associated with an unknown conductivity ($\Omega_{external}$) since it varies from patient to patient and between different regions in the cardiac chamber. This local parameterized surface 276 and the conductivity values ($\Omega_{blood}$ and $\Omega_{external}$) constitute a local forward model used in the inverse solver. This model aims to reconstruct the shape and value of the conductivity distribution. This inverse problem is nonlinear and requires the use of an iterative solver. The inverse solver is an optimizer that determines both the surface's parameters as well as the unknown external conductivity ($\Omega_{external}$). The choice of the local parameterized surface 276 is only limited by its number of parameters or degrees of freedom. For example, a fully parameterized 3D ellipsoid introduces nine degrees of freedom: three axial parameters and six parameters for rigid body translation and rotation. It is also possible to use polynomial representation, Bezier, NURBS or curvilinear finite elements to represent the parameterized surface 276.

Figure 6:
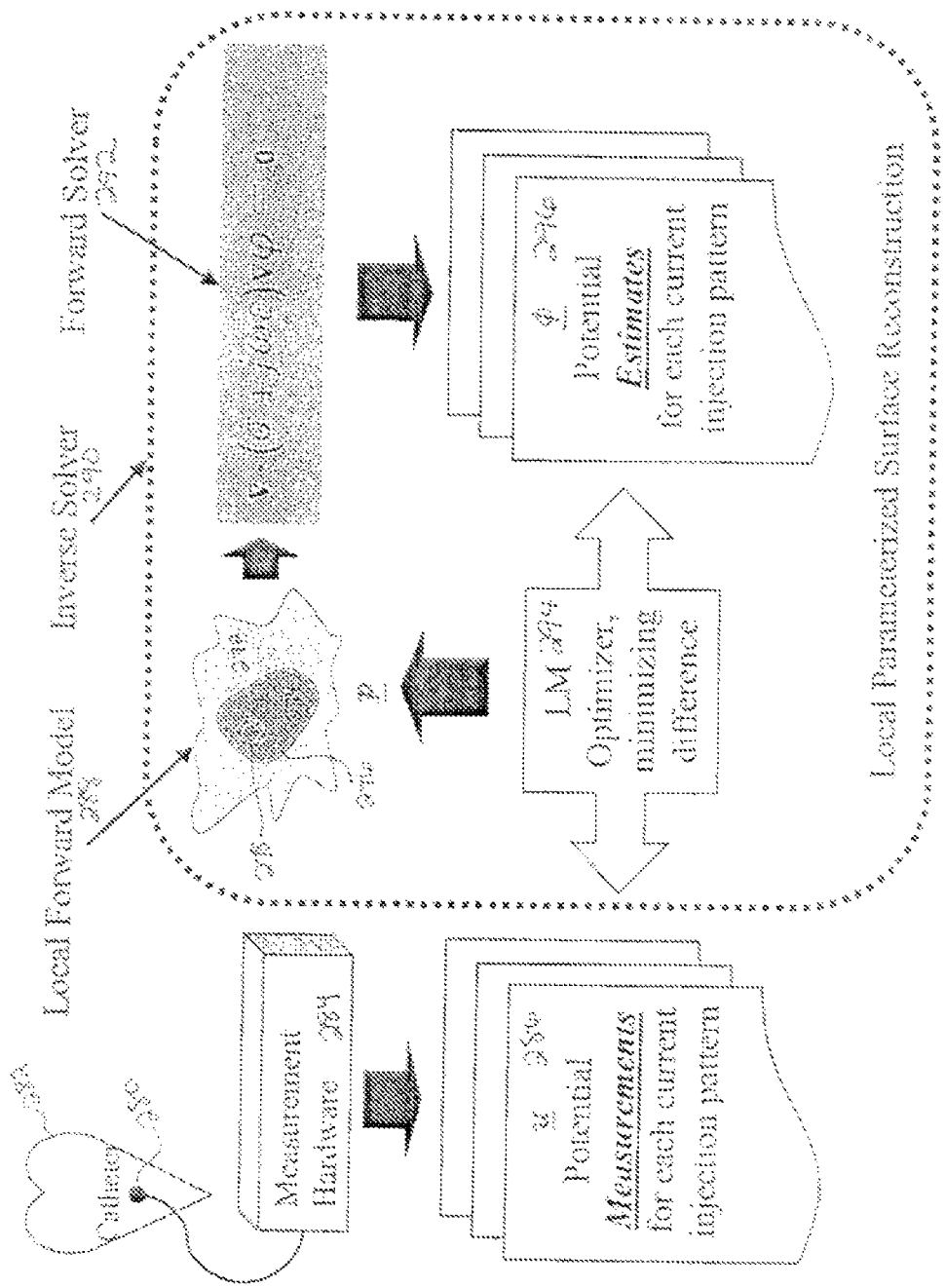
FIG. 6 is a schematic diagram of a process for determining a parameterized surface.

FIG. 6 shows a system and method for generation of a local parameterized surface including the measurement hardware 284 along with the inverse solver 290 (e.g., software) which reconstructs the local parameterized surface 276.

The measurement hardware 284 is connected to a catheter 280 placed within a patient's heart 282. The measurement hardware 284 collects potential measurements and electrode location 286 from the catheter 280. The inverse solver 290 uses these potential measurements and electrode location information 286 in the determination of the local parameterized surface.

The inverse solver 290 utilizes a search algorithm in the parameter-domain in order to minimize the difference between the measured electrode-potentials (e.g., potential measurements 286) provided by the measurement hardware 284 and the estimates of the electric potential field 296, provided by the local forward model 288. These later samples are taken at the corresponding locations of the measuring electrodes on catheter 280. An exemplary minimization equation is shown below:

$$\min_{p} \|\underline{u} - \underline{\phi}(\underline{p})\|_2^2$$

Where $\underline{u}$ is the vector of measured electrode potentials 286. $\underline{\phi}$ is the vector of potential samples predicted by the forward model 296 and dependent on φ, which is the vector of various parameters of the forward model 288 itself. During the measurement phase it is assumed that neither the location nor the orientation of the catheter is changing significantly, therefore the local forward model 288 assumes steady position and orientation of the catheter 280. Both the measured potentials 286 and predicted potential values 296 can be arranged in structured vectors and so the measure of difference can be defined by the sum of squares of corresponding differences. Minimization problems of this type can be efficiently solved by the Levenberg-Marquardt (LM) method (e.g., using LM optimizer 294). The LM algorithm is formulated in terms of the residual vector and the first derivative of this vector, which is called the Jacobian. During the search for the optimal parameter values, the forward solver 292 repeatedly solves for the ever changing local forward model 288. The solution of the forward model 288 is governed by the Laplace's equation and provides the potential distribution for the domain defined by the local forward model 288, and so the potential values at the electrodes of the model-catheter as well. Different approximation methods such as Spherical Harmonics, Finite Elements, Boundary Elements or Multiple MultiPoles can be used to discretize Laplace's equation, resulting in an algebraic linear equation system in Equation 2.

$$Kx = f \qquad \text{(Equation 2)}$$

The solution of the linear equation system provides the values for the so called degree of freedoms (x), which in turn along with the corresponding field approximation functions Constitute the overall approximation of the electrical field K is the so called stiffness matrix collecting the contribution from the discretized differential operator, f represents excitation due to sources or boundary conditions.

The LM algorithm requires the derivatives of the residual vector in terms of the parameters of the local forward model. There are two possible approaches to obtaining the derivatives. They can be estimated using finite differentiation techniques, or using a direct differentiation method in the forward solver. In testing the direct approach was shown to be superior in terms of speed and accuracy due to the larger approximation error of the finite differentiation technique.

Valid Patch Selection

After successful optimization of the local parameterized surface 276, the local parameterized surface 276 is expected to be similar or partially similar to a portion of the true chamber boundary (e.g., as shown above in FIGS. 4A-4E). The region of the local parameterized surface that approximates the chamber boundary with sufficient accuracy is described herein as a valid patch. The rest of the local parameterized surface bears no significant influence on the electric field-pattern predicted by the local forward model. Such surface regions may be present in a relatively distant location from the catheter because, as explained earlier, the injected current pattern will not diffuse sufficiently into those far regions and so the field pattern will not be influenced by features located in those regions.

The parts of the local parameterized surface that are less likely to approximate the true chamber boundary are filtered out so only the valid patches remain that are most responsible for the field pattern measured by the electrodes and reconstructed by the optimized local forward model. The final boundary of the chamber is reconstructed by forming a surface e.g., a triangular-mesh based surface) so that it fits the set of previously obtained valid patches while also maintaining reasonable surface-smoothness properties.

The selection of the valid patches can be a mostly a heuristic procedure. In some embodiments, the local parameterized surface is subdivided and only certain regions are kept for the final reconstruction step as valid patches. The main criterion for selecting the valid patches is based on the strength of a distortion field. The distortion field is the difference between the field in presence of inhomogeneity and the field which corresponds to the homogenous medium. The higher the strength of the distortion field on a certain location of the local parameterized surface, the more the field pattern resulting on the PME is sensitive to the location and orientation of that surface location. Therefore, the distortion field strength is believed to be a good indicator of the surface location's validity (strength of influence). The main criterion is then simply to select patches that exhibit higher distortion field than a certain threshold ($df_{threshold}$). This criterion is then combined with additional side-criteria in order to increase the certainty of the decision. In some embodiments, two side-criteria are used: one criteria is based on the distance of the surface location from the center of the catheter, and the other criteria is based on the final residual error of the LM optimization. It should be noted that additional quantities may also contribute to the accuracy of the filtering process. The side criteria are formulated and combined via the fuzzy logic approach.

Figure 7:
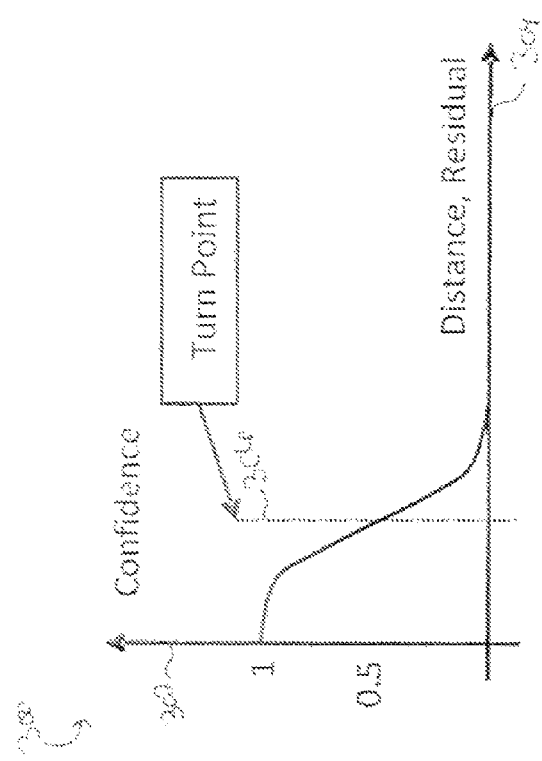
FIG. 7 is an exemplary graph of a confidence model.

FIG. 7 shows an exemplary graph 300 of "Membership functions" of "confidence" in which the x-axis 304 represents the distance or residual while the y-axis 302 represents the confidence that can be used which can be represented by:

$$C(x, t, \alpha) = \frac{1}{1 + e^{\alpha(x-z)}}$$

Where t and α are parameters of the membership function; t is the turn-point 306 and α determines the slope of the membership function at the turnpoint 306.

After proper normalization of the quantities involved in the side criteria, the evaluation of the membership functions result in confidence factors; for each criterion ($C_{residual}$ and $C_{distance}$). These factors are then used as multipliers of the distortion field strength (df) in the final acceptance criterion for valid patch selection:

$$df \times C_{residual} \times C_{distance} > df_{threshold} \qquad \text{(Equation 3)}$$

Once the above criterion is satisfied for a surface location, the surface location will become a candidate for selection for a valid patch. The final set of surface locations is limited as well, therefore only those locations providing highest values for the left hand side are selected for the final reconstruction.

The LM residual is expected to be smaller when the optimization is more successful and therefore the local parameterized surface is expected to approximate the chamber boundary better. For this reason, smaller values for the LM residual should produce higher confidence levels: one or close to one. Increasing residual, on the other hand, should eventually switch the corresponding confidence level down to zero. In order to establish what "small" is, the LM residual is normalized. This normalization is such that when the local forward model is the homogenous case, the corresponding normalized residual would be exactly one. In other words, the residual measures how much the distortion field is reconstructed by the optimized local forward model at the PME compared to the homogenous case, which is regarded as complete lack of reconstruction. The normalization described here is only the first step to make sure the membership function produces meaningful confidence levels. The missing additive is the parameter of the membership function itself, called turn-point. In some examples, for the LM residual a turn-point 306 of 0.05 is believed to be adequate. This is the normalized LM residual value, which produces confidence level of exactly one half. The appropriate α for this criteria is believed to be 80.

Figure 8:
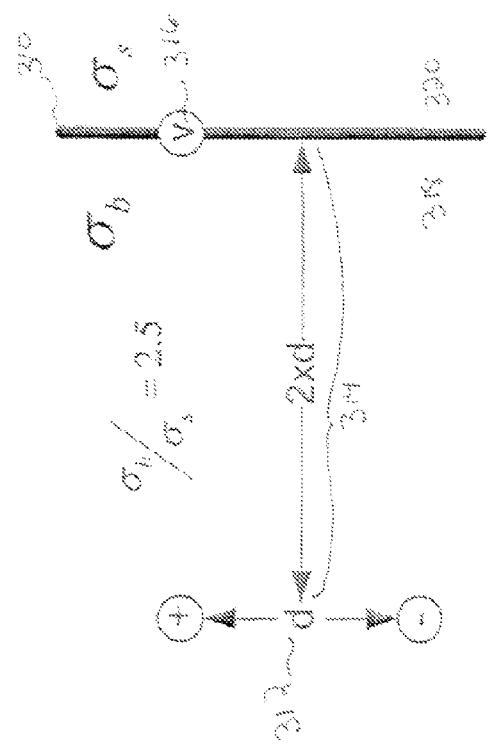
FIG. 8 is a schematic diagram of a dipole at a distance from an infinite plane.

As shown in FIG. 8, similar deductions can be given for the confidence level generated by the distance of the surface location relative to the catheter. For this criterion confidence should decrease as distance from the center of the catheter is increased. The surface location distance is normalized by expressing it relative to the radius of the catheter. For example, a reasonable turn-point is believed to be two times the catheter radius. For example, an appropriate α for this criteria is believed to be 0.5.

The threshold value in the selection criterion for the distortion field is derived from the analytical solution of a simple but relevant arrangement in order to account for possibly different catheter/dipole dimensions. The arrangement, as shown in FIG. 8, provides a dipole 312 with moment d assumed to be a distance 314 of two times the moment d from an infinite plane 310. The threshold value is set to be live times the value measured on the plane at point v, 316. The conductivity ratio between the side 318 of the plane where the dipole resides and the other side 320 of the plane is assumed to be 2.5.

For the subdivision of the local parameterized surface a surface triangulation is used as a mesh. The mesh is as uniform as possible, and the average size of the triangles should match the desired resolution for the filtering step. In some embodiments, an average edge length of 2 mm was found to be sufficient in balancing run-time with accuracy. Other subdivision of the local parameterized surface could also be used.

Electro-Anatomical Map ("EAM") Construction

The construction of electro-anatomical maps (EAMs) is a valuable tool for the diagnosis and therapy of a variety of cardiac related conditions including congestive heart failure, valve failure and arrhythmia. For the catheter ablation treatment of arrhythmia the reconstruction of anatomy provides both an understanding of the anatomical structure as well as the chamber boundary on which the three dimensional EAM map is constructed.

Full Chamber Map

The chamber boundary reconstructed using impedance measurements disclosed herein can be used as the surface onto which electrical information is projected. This electrical information may be collected using a contact scheme or non-contact scheme (e.g., as described in U.S. Pat. No. 7,505,810, the contents of which are hereby incorporated by reference). In the case of a non-contact scheme, both electrical and anatomical data may be collected simultaneously by the MEA catheter thus expediting the EAM generation process. Electrical information displayed on the EAM can include any of a number of isopotentials, bipolar maps, local activation time, voltage map, dominant frequency map, and the like.

Partial Chamber EAM Map

Figure 9:
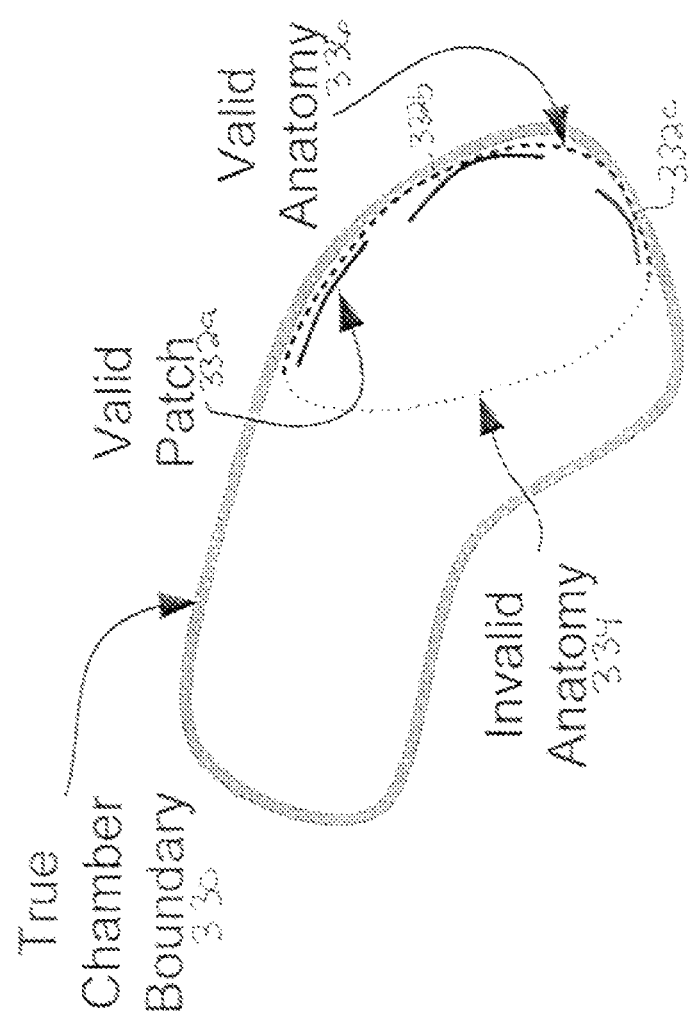
FIG. 9 is a schematic diagram of a partial boundary determination.

In some applications, it is necessary to construct only a partial EAM of the chamber (e.g., construct an EAM of less than the entire chamber). That is, to save procedure time, only a portion of the chamber known to participate in the arrhythmogenic mechanism needs to be provided on the EAM. For example, in the case of scar related ventricular tachycardia, only the scarred area and its immediate surrounding tissue may be required for clinical treatment. Such portion can represent under 25% of total chamber area and be collected with a limited number of catheter locations. For example, less than 10 catheter locations may be used to generate the partial EAM (e.g., 8 catheter locations or less, 6 catheter locations or less, 5 catheter locations or less, 4 catheter locations). In such case, as shown in FIG. 9, it is possible to construct a partial anatomy 336 by meshing a closed surface around the valid patches (e.g., patches 332a, 332b, and 332c). Since the surface 336 is not complete in this case, such closed mesh also contains areas 334 where no valid patches exist nearby. However, those are known from the valid patch selection process described above and marked invalid, invalid areas 334 in the mesh can be either transparent or rendered differently (e.g. show only mesh edges and render mesh faces transparent, display gray, make semi-transparent).

Once the partial chamber anatomy is constructed, electrical information can then be displayed only on the valid areas (e.g., area 336) of the anatomy using either a non-contact or contact scheme. It is important to note that the added information of valid and invalid zones is crucial to the construction of a partial EAM map. If invalid areas of the anatomy are not marked as such, the EAM may lead to wrong clinical interpretation. The information regarding the validity of the map provided with the impedance scheme is unavailable with other point collection schemes making partial maps more difficult to interpret.

Experimental Results

Figure 11:
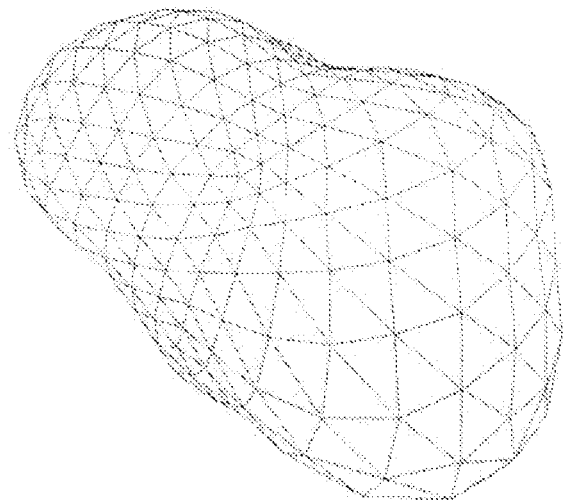
FIG. 11 is a schematic diagram of a curvilinear local parameterized surface.
Figure 10:
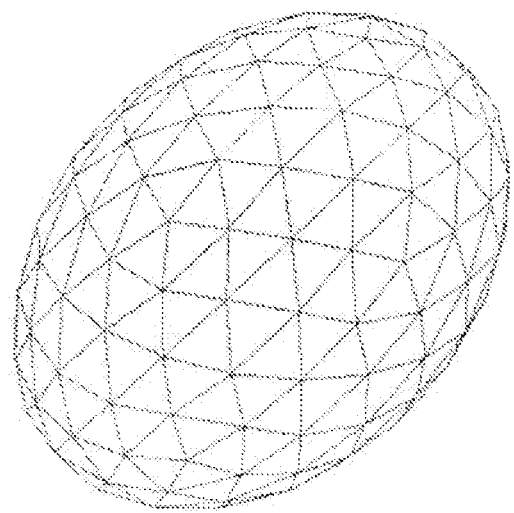
FIG. 10 is a schematic diagram of an ellipsoidal local parameterized surface.

FIGS. 10 and 11 show exemplary local parameterized surfaces. More particularly, FIG. 10 shows a ellipsoidal local parameterized surface with 9 degrees of freedom while FIG. 11 shows a curvilinear local parameterized surface with 18 degrees of freedom.

Figure 12:
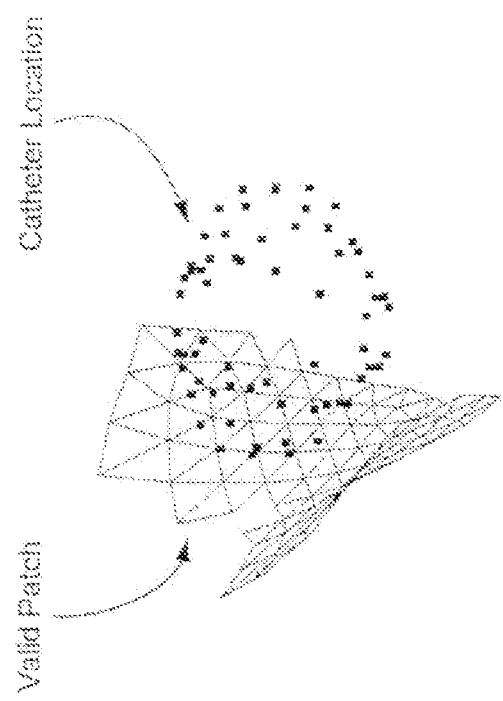
FIG. 12 is a schematic diagram of valid patches relative to a catheter location.

FIG. 12 shows valid patches detected relative to a catheter location.

Figure 13A:
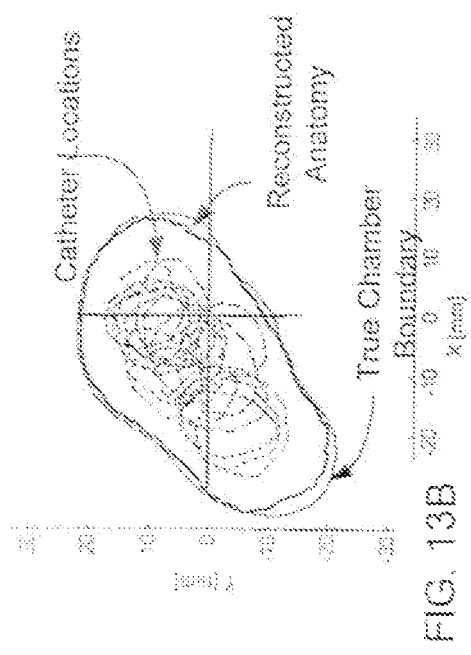
FIGS. 13A-13D show exemplary anatomical information.
Figure 13B:
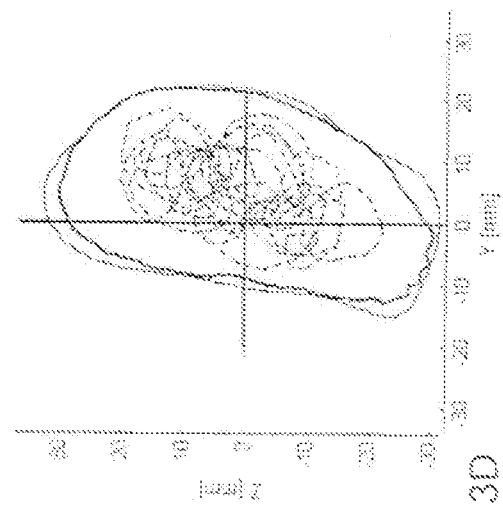
Figure 13C:
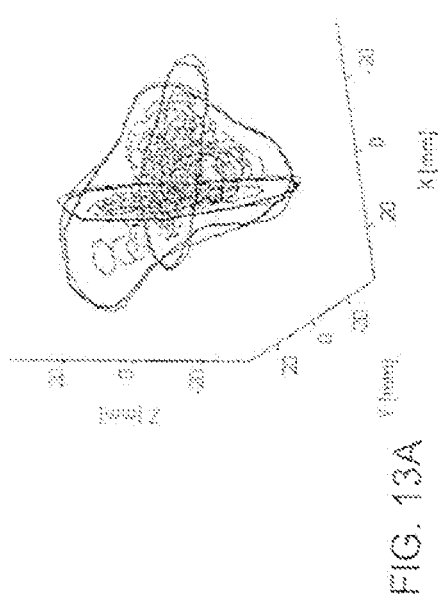
Figure 13D:
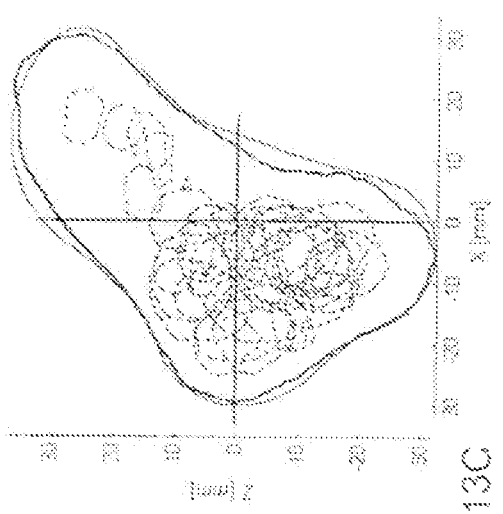

FIGS. 13A-D, provides multiple projections of an experiment reconstructing left ventricular ("LV") anatomy. FIG. 13A provides a three dimensional representation of the reconstructed anatomy of the LV, FIG. 13B provides a two dimensional representation of the reconstructed anatomy of FIG. 13A in the x-y plane, FIG. 13C provides a two dimensional representation of the reconstructed anatomy of FIG. 13A in the x-z plane, and FIG. 13D provides a two dimensional representation of the reconstructed anatomy of FIG. 13A in the y-z plane. The construction of the anatomy was accomplished using a MEA catheter with 6 CIE and 64 PME in a constellation similar to the one shown in FIG. 3. The catheter was moved to 51 locations within the left ventrical (LV). The synthetic measurements were generated using a Finite Element Method simulator. As shown in the figures, even areas that were sparsely sampled by the catheter are reasonably reconstructed.

Other Embodiments

In some aspects, the catheter used to generate the anatomical information and/or generate the EAM information can additionally include an electrode for delivering ablation energy for ablating tissue. As such, a single catheter can generate an EAM map (including generating the anatomical information used for the EAM map) and perform ablation of identified regions of the organ. It is believed that this can provide the advantage of limiting the number of catheters inserted into the organ of the patient. For example, an ablation procedure can involve mapping of electrical activity in the heart (e.g., based on cardiac signals), such as at various locations on the endocardium surface ("cardiac mapping"), to identify the site of origin of the arrhythmia followed by a targeted ablation of the site. A single catheter inserted into the patient's heart chamber can be used both to perform such cardiac mapping (including generating the anatomy of the heart) and to perform the ablation.

It should be understood that while this disclosure describes use of current injection and potential measurement, it is also possible to impart a known voltage on active electrodes and measure resultant potential or current. In effect, any interrogation of the medium performed by active electrodes which results in a current being diffused into the medium and a potential field imparted on it should be viewed and one and the same.

It should further be understood that while this invention describes the use of conductivity contrast, an impedance contrast comprising of both the conductivity contrast and/or permittivity contrast can also be used. In this case both the amplitude mid phase or I and Q components of the potential measured by the PME may be used by the same algorithm. Rather than estimating the conductivity alone, the complex impedance having both conductivity and/or permittivity can be computed. As the carrier frequency of the injected current is increased it is expected that permittivity contrast will increase and accounting for and using impedance contrast rather than conductivity alone is believed to improve accuracy.

The methods and systems described herein are not limited to a particular hardware or software configuration, and may find applicability in many computing or processing environments. The methods and systems can be implemented in hardware, or a combination of hardware and software, and/or can be implemented from commercially available modules applications and devices. Where the implementation of the systems and methods described herein is at least partly based on use of microprocessors, the methods and systems can be implemented in one or more computer programs, where a computer program can be understood to include one or more processor executable instructions. The computer program(s) can execute on one or more programmable processors, and can be stored on one or more storage medium readable by the processor (including volatile and non-volatile memory and/or storage elements), one or more input devices, and/or one or more output devices. The processor thus can access one or more input devices to obtain input data, and can access one or more output devices to communicate output data. The input and/or output devices can include one or more of the following: Random Access Memory (RAM), Redundant Array of Independent Disks (RAID), floppy drive, CD, DVD, magnetic disk, internal hard drive, external hard drive, memory stick, or other storage device capable of being accessed by a processor as provided herein, where such aforementioned examples are not exhaustive, and are for illustration and not limitation.

The computer program(s) can be implemented using one or more high level procedural or object-oriented programming languages to communicate with a computer system; however, the program(s) can be implemented in assembly or machine language, if desired. The language can be compiled or interpreted. The device(s) or computer systems that integrate with the processor(s) can include, for example, a personal computer(s), workstation (e.g. Sun, HP), personal digital assistant (PDA), handheld device such as cellular telephone, laptop, handheld, or another device capable of being integrated with a processor(s) that can operate as provided herein. Accordingly, the devices provided herein are not exhaustive and are provided for illustration and not limitation.

References to "a microprocessor" and "a processor", or "the microprocessor" and "the processor," can be understood to include one or more microprocessors that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network using a variety of communications protocols, and unless otherwise specified, can be arranged to include a combination of external and internal memory devices, where such memory can be contiguous and/or partitioned based on the application. Accordingly, references to a database can be understood to include one or more memory associations, where such references can include commercially available database products (e.g., SQL. Informix, Oracle) and also proprietary databases, and may also include other structures for associating memory such as links, queues, graphs, frees, with such structures provided for illustration and not limitation.

Accordingly, other embodiments are within the scope of the following claims.

What is claimed is:

1. A method comprising:
    inserting a catheter into a heart, the catheter comprising three or more electrodes;
    causing current to flow between at least some of the three or more electrodes and measuring an electrical signal, generated from the current flow, at each of one or more of the three or more electrodes;
    determining a representation of a chamber anatomy structure of at least a portion of the heart based on the measured electrical signals; and
    displaying at least a portion of the determined representation of the chamber anatomy structure with a first visual indicia indicative of areas having a distortion field and a confidence measure satisfying a threshold and a second visual indicia indicative of areas having a distortion field and a confidence measure that does not satisfy the threshold, the confidence measure being based at least in part on a proximity of the three or more electrodes on the catheter to a portion of the surface of the heart.

2. The method of claim 1, further comprising:
    measuring cardiac signals at electrodes of the three or more electrodes in response to electrical activity in the heart;
    determining physiological information based on the measured cardiac signals;
    displaying the physiological information on the determined representation of the chamber anatomy structure in the areas having the distortion field and the confidence measure satisfying the threshold; and
    prohibiting display of the physiological information on the determined representation of the chamber anatomy structure in the areas having the distortion field and the confidence measure that does not satisfy the threshold.

3. The method of claim 1, wherein displaying at least a portion of the determined representation of the chamber anatomy structure comprises displaying a mesh having a plurality of faces with faces of the mesh being opaque for the determined areas of the surface corresponding to the areas having the distortion field and the confidence measure satisfying the threshold and transparent, gray, or semi-transparent for other areas of the surface.

4. The method of claim 1, wherein displaying at least a portion of the determined representation of the chamber anatomy structure comprises displaying a mesh having a plurality of faces with faces of the mesh being opaque for the determined areas of the surface corresponding to the areas having the distortion field and the confidence measure satisfying the threshold and transparent, gray, or semi-transparent for the areas having the distortion field and the confidence measure that do not satisfy the threshold.

5. The method of claim 1, wherein displaying at least a portion of the determined representation of the chamber anatomy structure comprises displaying a mesh having a plurality of faces and applying the first visual indicia to faces of the mesh for the determined areas having the distortion field and the confidence measure satisfying the threshold and applying the second visual indicia to faces of the mesh for the areas of the surface not corresponding to the areas having the distortion field and the confidence measure that do not satisfy the threshold.

6. The method of claim 1, wherein the first and second visual indicias differentiate valid areas of the surface corresponding to the endocardial boundary from other areas of the surface.

7. The method of claim 1, further comprising:
measuring cardiac signals at electrodes of the three or more electrodes in response to electrical activity in the heart;
determining physiological information based on the measured cardiac signals; and
displaying at least some of the physiological information.

8. A method comprising:
inserting a catheter into a heart, the catheter comprising three or more electrodes;
for each of a plurality of catheter locations, causing current to flow between at least some of the three or more electrodes and measuring an electrical signal, generated from the current flow, at each of one or more of the three or more electrodes;
generating a representation of a chamber anatomy structure of at least a portion of the heart based on locations of the catheter and the electrical signal measurements, the generation being based at least in part on a data selection criteria associated with a proximity of the three or more electrodes on the catheter to a portion of the surface of the heart; and
displaying at least a portion of the determined representation of the chamber anatomy structure.

9. The method of claim 8, further comprising determining the proximity of the three or more electrodes on the catheter to a portion of the surface of the heart based at least in part on the measured electrical signals.

10. The method of claim 8, further comprising:
for each of the plurality of catheter locations, determining a local surface of at least a portion of the heart based on the measured electrical signals; and
determining valid and invalid areas of the local surface based on a determined distance between the catheter and the surface of the heart, the valid areas having determined distances between the catheter and the surface that are less than a threshold distance;
wherein determining the representation of the chamber anatomy structure comprises determining the representation of the chamber anatomy structure based on multiple ones of the valid areas of the local surfaces.

11. The method of claim 8, further comprising:
measuring cardiac signals at electrodes of the three or more electrodes in response to electrical activity in the heart;
determining physiological information based on the measured cardiac signals; and
displaying the physiological information.

12. The method of claim 11, wherein the determination of the representation of the chamber anatomy structure accounts for a change in conductivity at the cardiac chamber boundary.

13. The method of claim 12, wherein the determination of the representation of the chamber anatomy structure accounts for a first conductivity inside the cardiac chamber boundary and a second conductivity outside the cardiac chamber boundary.

14. The method of claim 8, wherein determining the representation of the chamber anatomy structure comprises determining the representation of the chamber anatomy structure based at least in part on impedance information generated based on the measured signals.

15. The method of claim 14, wherein the impedance information is based on a conductivity or permittivity contrast between blood and surrounding tissue.

16. The method of claim 14, wherein the impedance information comprises complex impedance information based on both a permittivity contrast and a conductivity contrast between blood and surrounding tissue.

17. The method of claim 8, wherein determining the representation of the chamber anatomy structure comprises, determining a closed and parameterized surface based on the measured signals, the surface representing a surface at which the conductivity value changes.

18. The method of claim 17, wherein the surface provides a boundary between a region represented by a first conductivity inside the surface and a region represented by a second conductivity outside the surface, the first conductivity being different from the second conductivity.

19. The method of claim 17, wherein determining the representation of the chamber anatomy structure further comprises, for each of the plurality of catheter locations determining a surface and selecting one or more regions of the surface corresponding to an expected boundary of the heart.

20. A system comprising:
a catheter comprising two or more electrodes configured to inject a current and to measure electrical signals from the injected current;
a processing unit configured to determine a representation of a chamber anatomy structure of at least a portion of the heart based on the measured electrical signals; and
a display unit configured to send a signal to a display device to cause the display device to display at least a portion of the determined representation of the chamber anatomy structure with a first visual indicia indicative of areas having a distortion field and confidence measure satisfying a threshold and a second visual indicia indicative of areas having a distortion field and confidence measure that does not satisfy the threshold, the confidence measure being based at least in part on a proximity of electrodes on the catheter to a portion of the surface of the heart.

21. The system of claim 20, wherein the processing unit is further configured to determine physiological information based on measured cardiac signals.

22. The system of claim 20, wherein the display unit is further configured to cause the display device to:
display physiological information on the determined representation of the chamber anatomy structure in the areas having the distortion field and confidence measure satisfying the threshold; and
prohibit display of the physiological information on the determined representation of the chamber anatomy structure in the areas having the distortion field and confidence measure that does not satisfy the threshold.

23. The system of claim 20, wherein the display unit is further configured to cause the display device to display a mesh having a plurality of faces with faces of the mesh being opaque for the determined areas of the surface corresponding to the areas having the distortion field and confidence measure satisfying the threshold and transparent, gray, or semi-transparent for other areas of the surface.

24. The system of claim 20, wherein the display unit is further configured to cause the display device to display a mesh having a plurality of faces with faces of the mesh being opaque for the determined areas of the surface corresponding to the areas having the distortion field and confidence measure satisfying the threshold and transparent, gray, or semi-transparent for the areas having the distortion field and confidence measure that does not satisfy the threshold.

25. The system of claim 20, wherein the display unit is further configured to cause the display device to display a mesh having a plurality of faces and applying the first visual indicia to faces of the mesh for the determined areas having the distortion field and confidence measure satisfying the threshold and applying the second visual indicia to faces of mesh for areas of the surface not corresponding to the areas having the distortion field and confidence measure that does not satisfy the threshold.

26. The system of claim 20, wherein the first and second visual indicias differentiate valid areas of the surface corresponding to the endocardial boundary from other areas of the surface.

27. A system comprising:
a catheter comprising two or more electrodes configured to inject a current and to measure electrical signals from the injected current;
a processing unit configured to determine a representation of a chamber anatomy structure of at least a portion of the heart based on locations of the catheter and the electrical signal measurements, the generation being based at least in part on a data selection criteria associated with differences between an electric field in the presence of an inhomogeneity and an homogeneous medium, and a proximity of the two or more electrodes on the catheter to a portion of the surface of the heart; and
a display unit configured to send a signal to cause a display device to display at least a portion of the determined representation of the chamber anatomy structure.

28. The system of claim 27, wherein the processing unit is further configured to determine the proximity of the two or more electrodes on the catheter to a portion of the surface of the heart based at least in part on electrical signal measurements.

29. The system of claim 27, wherein the processing unit is further configured to:
for each of the plurality of catheter locations, determine a local surface of at least a portion of the heart based on the measured electrical signals;
determine valid and invalid areas of the local surface based on a determined distance between the catheter and the surface of the heart, the valid areas having determined distances between the catheter and the surface that are less than a threshold distance; and
determine the representation of the chamber anatomy structure based on multiple ones of the valid areas of the local surfaces.

30. The system of claim 27, wherein the processing unit is further configured to:
determine physiological information based on measured cardiac signals; and
display the physiological information on the representation of the chamber anatomy structure.

31. The system of claim 27, wherein the processing unit is further configured to determine the representation of the chamber anatomy structure by accounting for a change in conductivity at the cardiac chamber boundary.

32. The system of claim 27, wherein the processing unit is further configured to determine the representation of the chamber anatomy structure by being based at least in part on impedance information generated based on the measured signals.

33. The system of claim 32, wherein the impedance information is based on a conductivity contrast or permittivity contrast between blood and surrounding tissue.

34. The system of claim 32, wherein the impedance information comprises complex impedance information based on both a permittivity contrast and a conductivity contrast between blood and surrounding tissue.

* * * * *